(12) United States Patent
Kwok et al.

(10) Patent No.: US 11,547,356 B2
(45) Date of Patent: Jan. 10, 2023

(54) WEARABLE DEVICE FOR HEALTHCARE AND METHOD THEREOF

(71) Applicant: Belun Technology (IP) Company Limited, Shatin (HK)

(72) Inventors: Ka Cheung Kwok, Shatin (HK); Wang Kin Fung, Shatin (HK); Luis Ng, Shatin (HK); Ngok Man Sze, Shatin (HK); Kwan Wai To, Shatin (HK)

(73) Assignee: BELUN Technology (IP) Company Limited, Shatin (HK)

( * ) Notice: Subject to any disclaimer, the term of this patent is extended or adjusted under 35 U.S.C. 154(b) by 175 days.

(21) Appl. No.: 16/887,959

(22) Filed: May 29, 2020

(65) Prior Publication Data
US 2020/0375538 A1 Dec. 3, 2020

Related U.S. Application Data

(60) Provisional application No. 62/856,465, filed on Jun. 3, 2019.

(51) Int. Cl.
*A61B 5/1455* (2006.01)
*A61B 5/00* (2006.01)

(52) U.S. Cl.
CPC .......... *A61B 5/6826* (2013.01); *A61B 5/1455* (2013.01); *A61B 5/6838* (2013.01); *A61B 5/14551* (2013.01); *A61B 5/4806* (2013.01); *A61B 2562/0238* (2013.01)

(58) Field of Classification Search
CPC .............. A61B 5/1455; A61B 5/14551; A61B 5/14552; A61B 5/6826; A61B 5/6838; A61B 2562/0238
See application file for complete search history.

(56) References Cited

U.S. PATENT DOCUMENTS

| | | | |
|---|---|---|---|
| 6,213,952 B1* | 4/2001 | Finarov | A61B 5/14552 600/310 |
| 6,321,100 B1* | 11/2001 | Parker | A61B 5/14552 600/340 |
| 2018/0132789 A1* | 5/2018 | Chen | A61B 5/1455 |

* cited by examiner

*Primary Examiner* — Eric F Winakur
(74) *Attorney, Agent, or Firm* — Juan Carlos A. Marquez; Marquez IP Law Office, PLLC

(57) ABSTRACT

A wearable device for healthcare and a method thereof, wherein the device is worn on a finger for measuring the health data of the user, including but not limited to, the heart rate, blood oxygen saturation, etc. The wearing size of the device is adjustable for different sizes of fingers. In one embodiment, the device includes a main body at least partially worn on a digit of a user; at least one physiological sensor attached to the main body for detecting physiological information; and at least two branches coupled to the main body for holding the digit while reducing the movement of the device. At least a part of at least one branch is changeable such that the wearing size of the device is adjustable for different sizes of digits. In another embodiment, at least a part of at least one branch is movable such that the wearing size of the device is adjustable for different sizes of digits.

11 Claims, 26 Drawing Sheets

WEARABLE DEVICE FOR HEALTHCARE AND METHOD THEREOF

This application claims priority to U.S. Provisional Application No. 62/856,465 filed on Jun. 3, 2019, the entire disclosure and contents of which is hereby incorporated by reference.

FIELD OF INVENTION

This invention relates to a medical device for health data measurement, and more particularly, to a physiological measurement device with adjustable wearing size.

BACKGROUND

Nowadays, wearable device for health data measurement is becoming a very popular trend within the healthcare industry and is increasingly being used on a more regular basis. In one main application field, many wearable/portable devices are designed to measure the health data of the user, e.g., blood oxygen saturation, during the sleep to monitor any sleep disorder exists for diagnosis and treatment in advance. Generally, the wearable device is designed to be worn by the user during the whole night for long time monitor. In order to relieve the long-term wearing load, increase the user's comfortability during the long-term wearing and improve the user's sleep quality, one solution is to wear a sensor device on the user's finger for detecting physiological information during sleep.

However, since different users have different finger sizes, the diameter of which normally varies from 15.7 mm to 21.2 mm, the wearable device should be prepared with many sizes to fit for different finger sizes. For those wearable devices which are commonly used in the hospital for monitoring the patients' physiological information, it's inconvenient to reserve many sizes of the wearable devices for different patients.

Under such condition, the wearable device, especially worn on the fingers, with adjustable sizes is demanded for mass application. In one existing solution, the wearing size of the wearable device could be adjusted by extending the wearing body with embedded screws, as disclosed by the prior art references CN105942680 and CN107969771. In another existing solution, the wearing size of the wearable device could be adjusted by adding an extending portion between two parts of the wearing body, as disclosed by the prior art references US20170006978 and JP03214654U. In still another existing solution, the wearing size of the wearable device could be adjusted by adding one or more flexible parts, e.g., springs, between the wearing body, as disclosed by the prior art references U.S. Pat. No. 5,943,882 and DE202006000690. In still another existing solution, the wearing size of the wearable device could be adjusted by inserting one or more shims between the wearing body and the user for reducing the ring size, as disclosed by the prior art references U.S. Pat. Nos. 6,354,106, 7,735,337, and 9,743,726B1. In still another existing solution, the wearing size of the wearable device could be adjusted by replacing the internal wearing body in different sizes, as disclosed by the prior art references U.S. Pat. No. 8,448,464 and US20180020980. In still another existing solution, the wearing size of the wearable device could be adjusted by mechanical process, e.g., to configure two ratchet elements at the connecting ends of the two arms of the wearing body so as to adjusting the size of the wearing body by adjusting the overlap ratio of the two ratchets, as disclosed by the prior art US20180338587A1.

However, for most of the above solutions the cost is relatively high, and the structure is not compact for long term wear. Some other solutions are not proper for long-term wear especially during the night. Due to the requirement from the doctor or nurse in the hospital to apply the wearable device on the different patients for detecting their physiological information during the whole night, it is necessary to develop an adjustable wearable device of which the wearing size could be easily changed and the whole structure is compact and comfortable for long-term wear.

BRIEF DESCRIPTION OF THE DRAWINGS

Advantages of the present invention will be apparent from the following detailed description of exemplary embodiments thereof, which description should be considered in conjunction with the accompanying drawings, in which.

SUMMARY OF THE INVENTION

Figure 1:
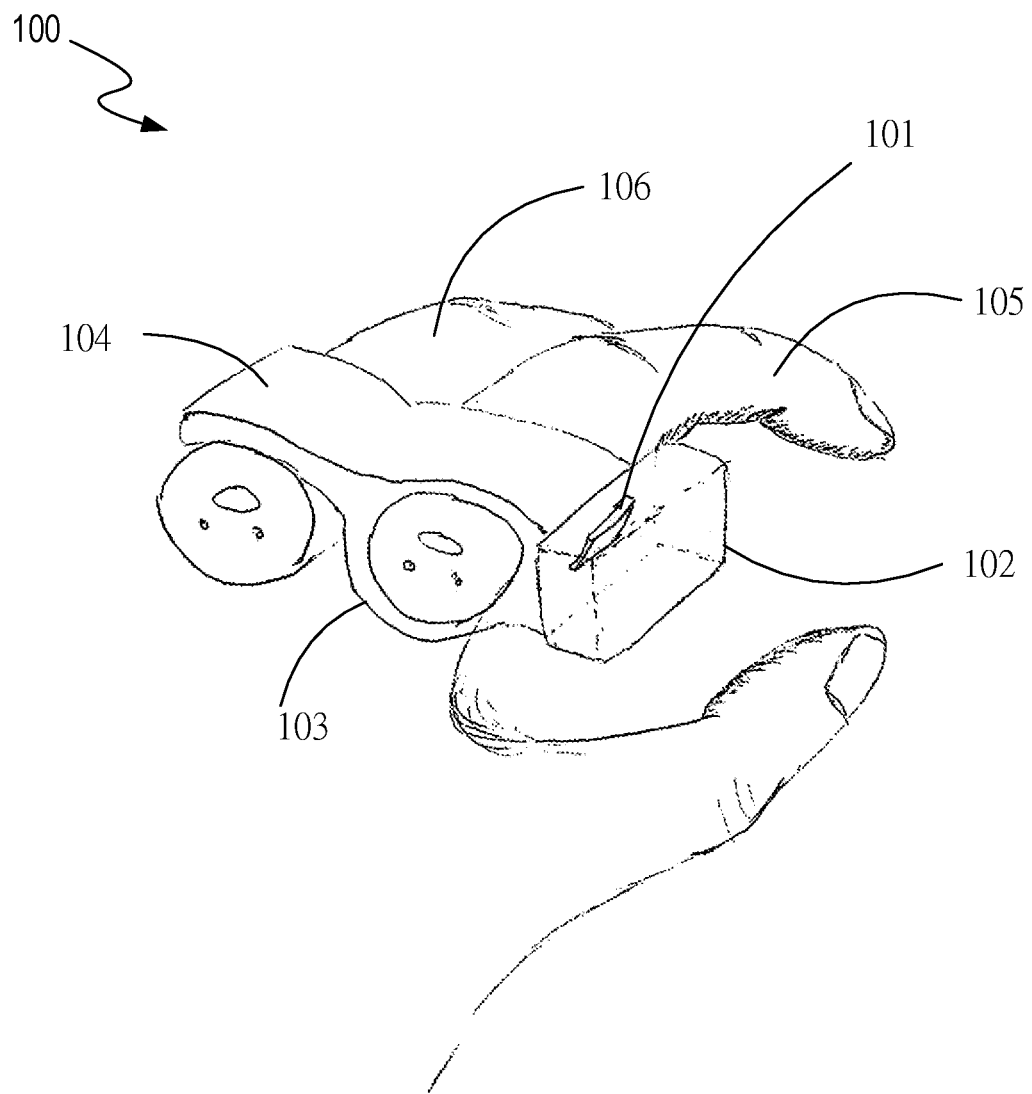
FIG. 1 illustrates a schematic drawing of a wearable device 100, according to one embodiment.

The present invention relates to a wearable device for healthcare and a method thereof. More specifically, the wearable device is worn on a finger for measuring the health data of the user, including but not limited to, heart rate, blood oxygen saturation, etc. The wearing size of the wearable device is adjustable for different sizes of fingers.

In one embodiment, a wearable device for detecting physiological information of a user comprises a main body configured to be at least partially worn on a digit of a user; at least one physiological sensor attached to the main body for detecting physiological information of the user through the digit; and at least two branches coupled to the main body for holding the digit while reducing the movement of the wearable device, wherein at least a part of at least one of the branches is changeable such that a wearing size of the wearable device is adjustable for different size of digits.

In another embodiment, a wearable device for detecting physiological information of a user, comprises a main body configured to be at least partially worn on a digit of a user; at least one physiological sensor attached to the main body for detecting physiological information of the user through the digit; and at least two branches coupled to the main body for holding the digit while reducing the movement of the wearable device, wherein at least a part of at least one of the branches is movable such that a wearing size of the wearable device is adjustable for different size of digits.

DETAILED DESCRIPTION

Reference will now be made in detail to the embodiments of the present invention. While the invention will be described in conjunction with these embodiments, it will be understood that they are not intended to limit the invention. The invention includes alternatives, modifications and equivalents covered within the scope of the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention. In the light of the foregoing background, it is an object of the present invention to provide a wearable device for monitoring health status of the user.

The following embodiments of the present invention describe an exemplary wearable device carried by a user for measuring physiological information of the user. In one embodiment, the wearable device is at least partially worn on a part of the user's body to monitor the health status of the user. In a preferred embodiment, the wearable device is at least partially worn on one or more digits of a limb to measure the physiological information, e.g., heart rate, heart rate variability, blood oxygen saturation, photoplethysmography (PPG) signal, and/or stress, of the user. In one embodiment, a digit of a limb represents, but is not limited to, a digit of a hand and/or a digit of a foot, e.g., a finger of a hand or a toe of a foot (hereinafter, simply referred to as a finger or fingers or a toe or toes). In a preferred embodiment, the wearable device is at least partially worn on a position near the finger root to monitor the user's health information. For example, the wearable device is at least partially worn on a proximal phalange of the finger, in one embodiment. In another preferred embodiment, the wearable device is worn on a user's index finger for easy and comfortable wear.

FIG. 1 illustrates a schematic drawing of a wearable device 100, according to one embodiment. Generally speaking, the wearable device 100 could be any shape as long as it satisfies the requirement of being able to be worn on the finger.

In one embodiment, the wearable device 100 comprises a main body 103 with an open loop in order to suit different sizes of fingers. Furthermore, the wearable device 100 comprises a sensor 101 being attached to the main body 103, and operable for sensing biological information of the user when the wearable device 100 is worn on a digit, e.g., a finger 105, and/or other similar positions of the user through the main body 103. The embodiment of FIG. 1 is for illustration purpose and the structure and wearing manner of the wearable device 100 is not limited to the embodiment. In one embodiment, the sensor 101 is an optical sensor that comprises a first light emitter, a second light emitter and at least one light detector. In one embodiment, the wavelength of the first light generated from the first light emitter is within the range of 850-1000 nm, e.g., IR light, and the wavelength of the second light generated from the second light emitter is within the range of 600-750 nm, e.g., visible light. The first/second light emitter emits the first/second light to a blood vessel in the finger and the light detector is operable to detect the first/second light reflected by the blood vessel in the finger. In one embodiment, the blood vessel may be an artery of the digit, e.g., the princeps pollicis artery which runs along the thumb, the radialis indicis artery which runs along the index finger, and/or the digital arteries which run along the other fingers. The detected first and/or second light signals, that carry health information of the user, is further used to calculate the health data of the user, e.g., a PPG signal, heart rate, heart rate variability, and blood oxygen saturation level, so as to determine the health status of the user. In one embodiment, the heart rate and heart rate variability are determined based on the PPG signal.

In one embodiment, the principle of the sensor 101 for measuring the blood oxygen saturation is based on the first and second light absorption characteristics of oxygenated and deoxygenated hemoglobin. Oxygenated hemoglobin absorbs more first light and allows more second light to pass through. Deoxygenated (or reduced) hemoglobin absorbs more second light and allows more first light to pass through. Based on the first/second light reflected by the blood vessel of the finger 105 and detected by the light detector, the $IN_2/IN_1$ ratio is calculated to determine the blood oxygen saturation, wherein $IN_1$ represents the intensity of the detected first light and $IN_2$ represents the intensity of the detected second light. Furthermore, the heart rate and heart rate variability of the user is able to be detected based on the first light. When the first light is reflected by the blood vessel of the finger 105, the intensity of the reflected first light will vary with the blood volume inside the blood vessel. Therefore, for each heartbeat, the blood volume inside the blood vessel will slightly change thereby altering the intensity of the first light that can be detected by the light detector. As such, the heart rate and heart rate variability can be determined according to the variation of the intensity of the detected first light signal. In an alternative embodiment, the first and second light emitters are integrated into one unit which is able to individually emit the first and second light based on a control signal. The embodiments of the sensor 101 are for illustration purpose and the lighting arrangement, including emitter and detector, is not limited to these embodiments.

Figure 2:
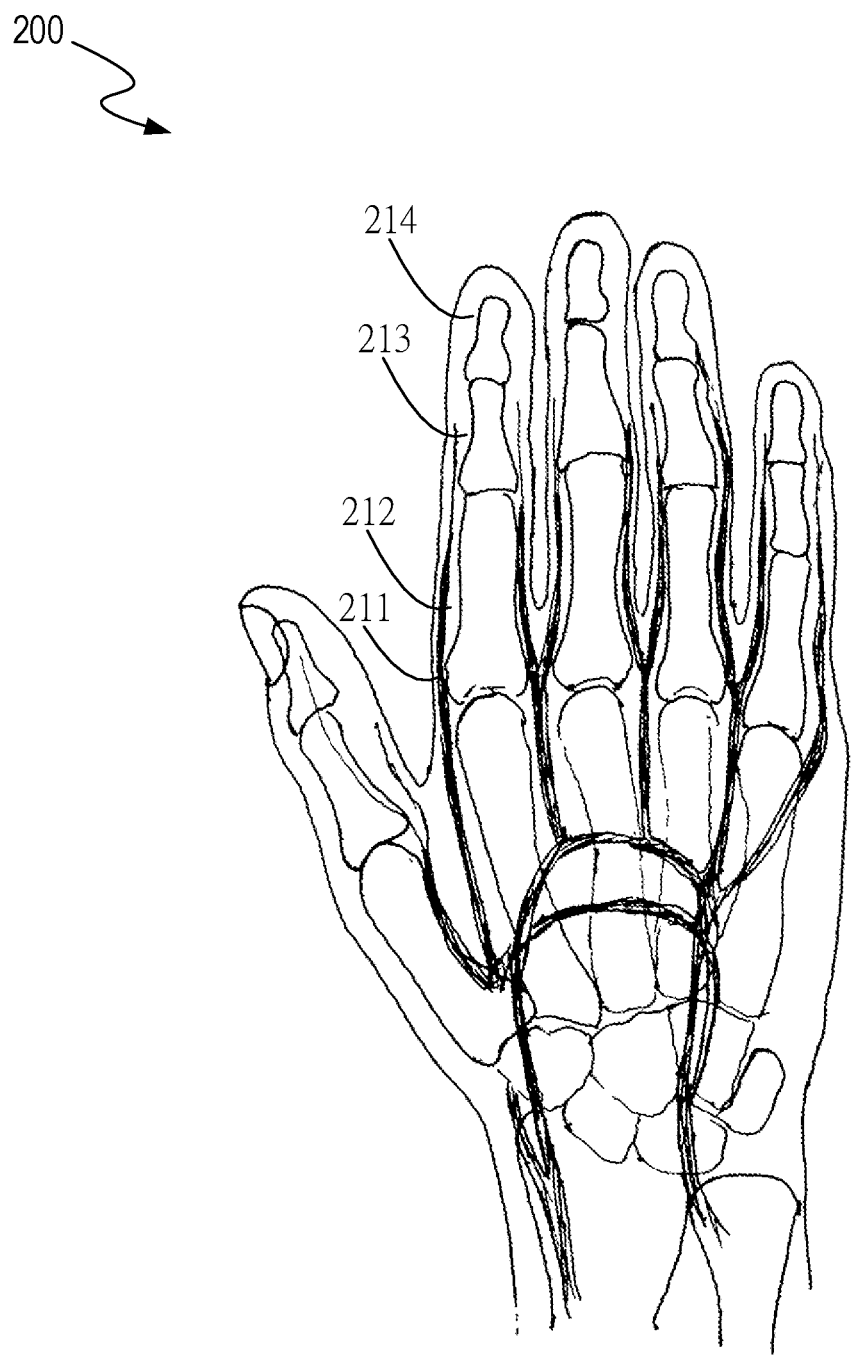
FIG. 2 illustrates a structure of a normal human hand 200.

FIG. 2 illustrates a structure of a normal human hand 200. FIG. 2 is described in combination with FIG. 1. As shown in FIG. 2, the main blood vessel is located near the lateral side of the fingers of the hand 200 with a slight offset to the palmar surface of the fingers. Conventionally, a wearable device is worn on the tip 214 of a finger because plentiful capillaries exist in the fingertip 214, such that the biological information is relatively easily detected. However, as mentioned before, to wear the wearable device on the fingertip is not comfortable, convenient or stable for long-term wear to continuously monitor the subject's health status. Therefore, it is preferred to wear the wearable device 100 on the middle 213 or proximal 212 part of the user's finger for more comfortable, convenient and stable extended wear. However, as compared with the fingertip 214, fewer capillaries exist in the middle or proximal part of the finger. In order to get more physiological information from the blood vessels of the finger, the sensor 101 is preferably positioned near the main blood vessel 211. In one embodiment, the sensor 101 is positioned near an artery of the finger for detecting the health information via the artery. During operation, it is important to fix the sensor 101 of the wearable device 100 close to the main blood vessel 211 to secure the accuracy of the measurement.

Figure 3:
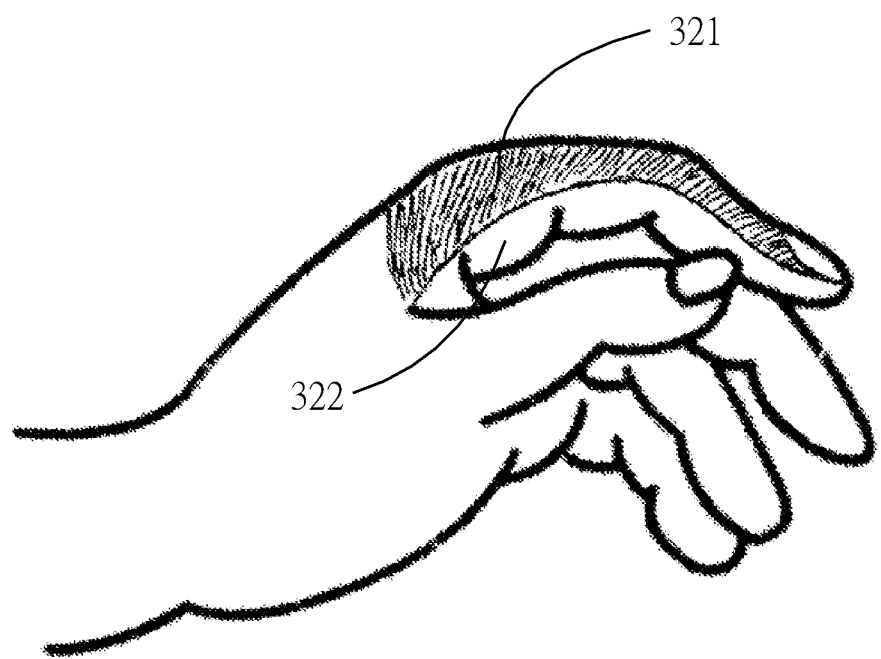
FIG. 3 shows the difference between skin colors of palmar and dorsal surfaces of human hands.

Furthermore, the skin color of the palmar surface 322 is typically lighter than the dorsal surface 321 of human hands, as illustrated in FIG. 3. And among different people, especially for different human races, the skin colors at the dorsal surface 321 of human hands are more variegated as comparing with the palmar surface 322 of hands. As commonly known, melanin is the primary determinant of skin color. The greater the amount of melanin in the skin, the darker the skin color. During operation, the light will be partially absorbed by the melanin of the skin. Further, the light absorption rate will increase with an increasing amount of the melanin in the skin. In other words, more light will be absorbed by darker skin while passing through it. Therefore, on the dorsal surface 321 of the finger, more light is absorbed than that on the palmar surface 322, and the absorption rate varies from person to person. Moreover, the absorption rates of the first light and second light are different due to their different wavelengths. In one embodiment, more second light whose wavelength is within the range of 850-1000 nm is absorbed by the melanin as compared with the first light whose wavelength is within the range of 600-750 nm. As described above, the blood oxygen saturation is calculated based on the first and second light absorption characteristics of oxygenated and deoxygenated hemoglobin. Therefore, due to the uncertain and uneven absorption rates of the first and second light at the dorsal surface 321 due to variations in human skin color, measurement accuracy of the sensor 101 will be significantly affected if positioned on the dorsal surface 321.

Figure 4:
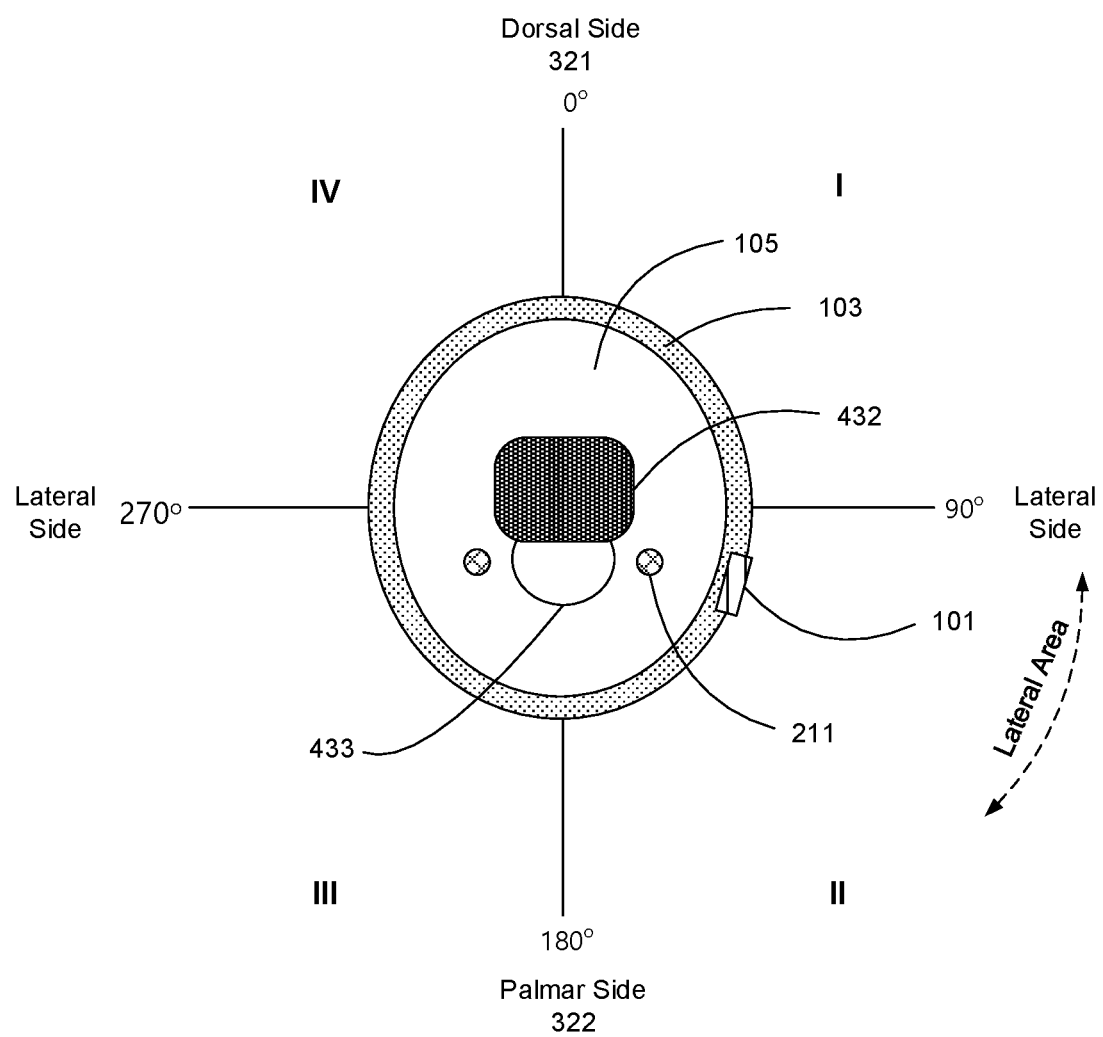
FIG. 4 illustrates the location range of the sensor 101 being arranged on the finger, in accordance with one embodiment of the invention.

In order to enhance the measurement accuracy and reduce the impact on the measurement accuracy as described above, the sensor 101 is preferably placed within a predetermined lateral area of the finger thereby being positioned close to the main blood vessel 211. In one embodiment, the lateral area is an area near the lateral side. In a specified embodiment, the lateral area is located on the palmer surface 322 of the finger and near the lateral side, as exemplarily specified by a circle 323. FIG. 4 illustrates the lateral area of the finger within which the sensor 101 is located, in accordance with one embodiment of the invention. FIG. 4 is described in combination with FIGS. 1-3. As shown in FIG. 4, the finger 105 mainly comprises bone 432, blood vessels including a main blood vessel 211, and tendons 433, wherein the main blood vessel 211 is located near the lateral side with a slight offset to the palmar surface 322. In one embodiment, in order to obtain more information from the main blood vessel 211, the sensor 101 is configured to be positioned adjacent to the palmer surface 322 and under the lateral side of the finger 105 (i.e., area II and/or III of FIG. 4). In a preferred embodiment, an angle range between the edge of the lateral area and the lateral side is from 20 degrees to 50 degrees, as the emitted and reflected light to/from the sensor 101 is closer to the main blood vessel 211.

Figure 5A:
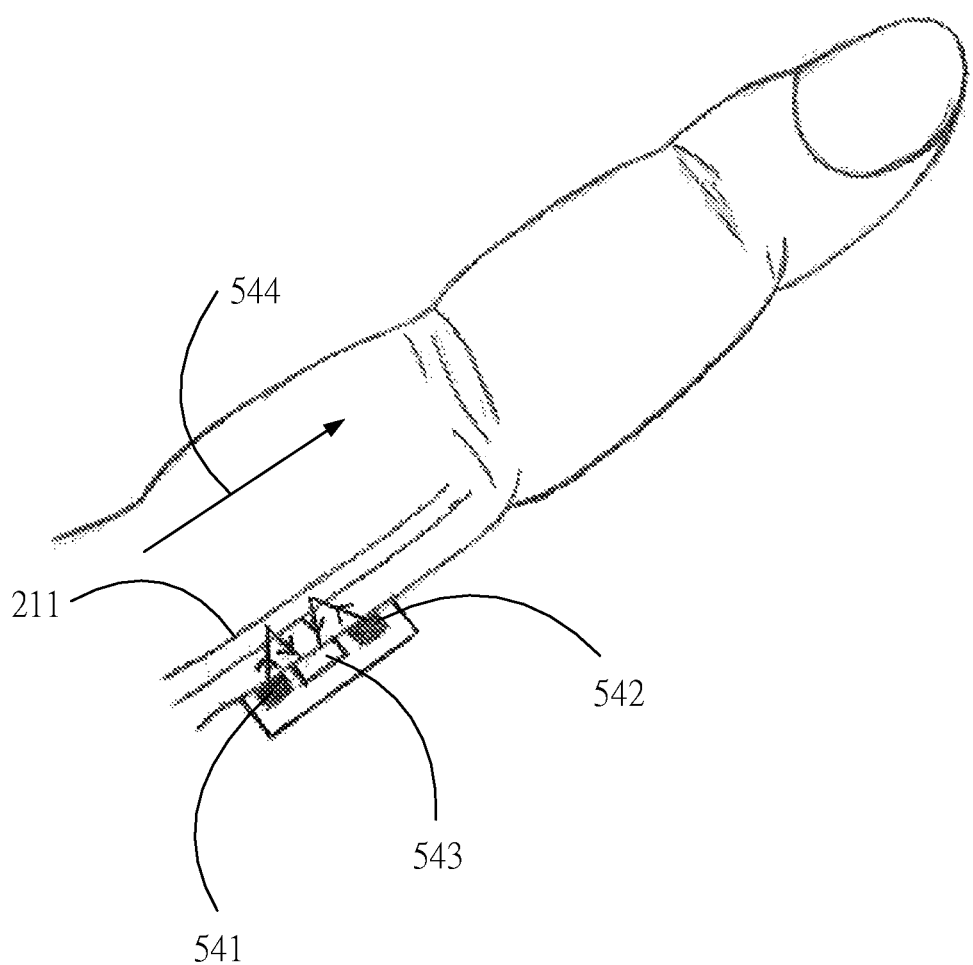
FIG. 5a illustrates a configuration manner of the sensor 101 with respect to a finger, in accordance to one embodiment.
Figure 5B:
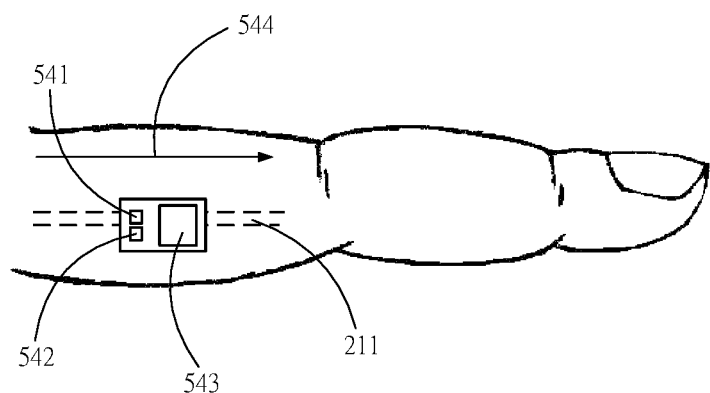
FIG. 5b illustrates another configuration manner of the sensor 101 with respect to a finger, in accordance with an alternative embodiment.

Furthermore, the sensor 101 is preferably placed along a longitudinal direction of the finger in order to minimize the effect on the light passing through the skin caused by uneven skin color along a latitudinal direction of the finger. The longitudinal direction is a direction substantially from finger root to fingertip (or vice versa). The latitudinal direction is substantially perpendicular to the longitudinal direction and extends around the finger. FIG. 5a illustrates a configuration of the sensor 101 with respect to a finger, in accordance with one embodiment. FIG. 5b illustrates another configuration of the sensor 101 with respect to a finger, in accordance with an alternative embodiment. FIGS. 5a and 5b are described in combination with FIGS. 1-4. As shown in FIG. 5a, the sensor 101 is placed along the longitudinal direction 544 of the finger. In a preferred embodiment, the sensor 101 is placed adjacent to the blood vessel 211 at a palmar surface 322 below the lateral side of the finger. More specifically, the sensor 101 comprises first and second light emitters 541 and 542 (or vice versa) and a light detector 543 placed along the longitudinal direction 544 and close to the blood vessel 211 in order to detect the health information of the user via the blood vessel 211. In a preferred embodiment, the distance between the first light emitter 541 and light detector 543 is substantially the same as the distance between the second light emitter 542 and the light detector 543. Referring to FIG. 5b, since the light emitters 541 and 542 are much smaller than the light detector 543, each of the light emitters 541 and 542 and the light detector 543 are arranged along the longitudinal direction 544 of the finger, wherein the first and second light emitters 541 and 542 are arranged at the same side of the light detector 543 while close to each other. In a preferred embodiment, the distance between the first light emitter 541 and the light detector 543 is substantially the same as the distance between the second light emitter 542 and the light detector 543. As can be understood by one skilled in the art, such details of a wearable device are merely examples, and the claimed subject matter is not so limited. For example, the first and second light emitters 541 and 542 may be arranged at any side of the light detector, and any one of the first and second light emitters 541 and 542 could be arranged above the other one.

Figure 5C:
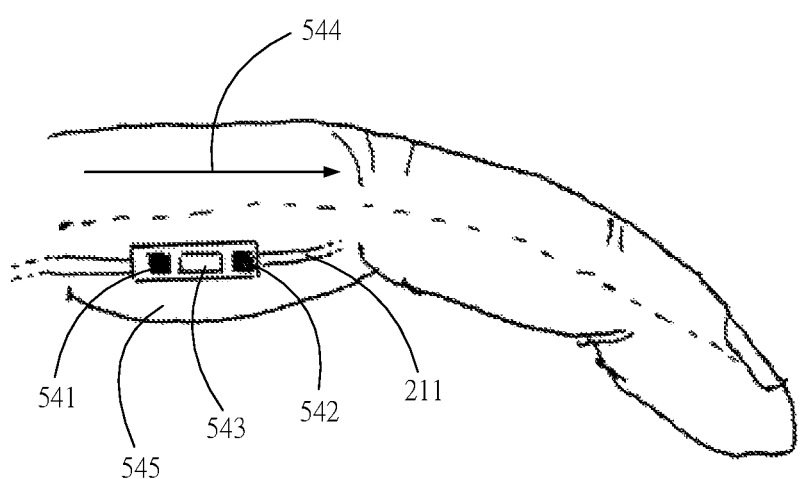
FIG. 5c illustrates less effect on the contact between the sensor 101 and the folded finger, in accordance with one embodiment of the invention.

As mentioned above, the absorption rate of the first and second light is significantly affected by the melanin in the dorsal surface 321 of the finger, which may affect the accuracy of the measurement. With the arrangement illustrated in FIG. 5a, the configuration of the sensor 101 is more compact at one side and the rotation tolerance, within the palmer surface 322, of the sensor 101 around the finger is enhanced. This is due to the light emitter and detector being arranged along the longitudinal direction and at the same level with respect to the latitudinal direction. As compared to the light emitter and detector being arranged along the latitudinal direction, if the sensor 101 rotates around the finger, there is greater tolerance for the light emitter and detector to be kept within the palmer surface during the rotation. Furthermore, since the light emitters and detector 541-543 are arranged along the longitudinal direction 544 at the palmer surface nearby the lateral side, when the finger is folded as shown in FIG. 5c, the impacted palmar surface 545 will not affect the contact between the sensor 101 and the finger skin.

In the embodiment of FIG. 1, the wearable device 100 may further include a matching unit 104 to guide the user to properly wear the wearable device 100 with the sensor 101 being positioned at the target location, and to reduce the rotation of the wearable device 100 around the finger 105 during long-term wear and measurement. In one embodiment, the matching unit 104 comprises at least one extending unit coupled to the main body 103, as shown in FIG. 1. In one embodiment, the extending unit comprises a wing configured at a lateral side of the main body 103. The material of the matching unit 104 may be rigid or elastic, depending upon the desired degree of fixation. When the wearable device 100 is worn on the finger 105, the finger 106 adjacent to the subject finger 105 is coupled with the matching unit 104 that helps to guide the user to properly wear the wearable device 100 and reduce rotation of the wearable device 100. In a preferred embodiment, the wearable device 100 comprises two extending units to hold the adjacent finger 106 for increased stability. The matching unit 104 is designed to correspond to the finger shape for long-term comfortable wear. In an alternative embodiment, the matching unit 104 comprises a loop with or without an opening and coupled to the main body 103. When the wearable device 100 is worn on the finger 105, the loop is configured to surround the adjacent finger 106 to guide the user to properly wear and minimize the rotation of the wearable device 100.

Figure 6A:
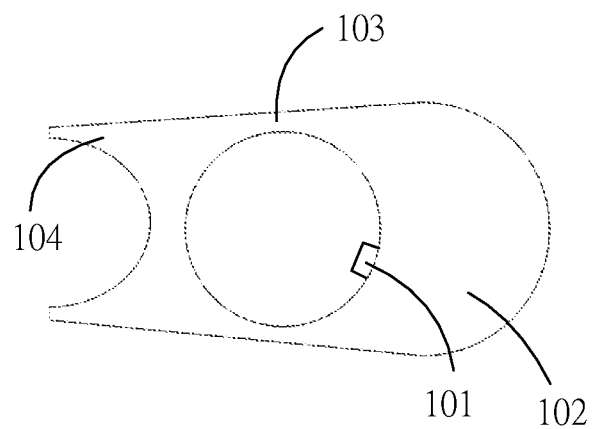
FIG. 6a-c illustrate three types of the wearable device 100 with different shapes of the matching unit 104, according to alternative embodiments.
Figure 6B:
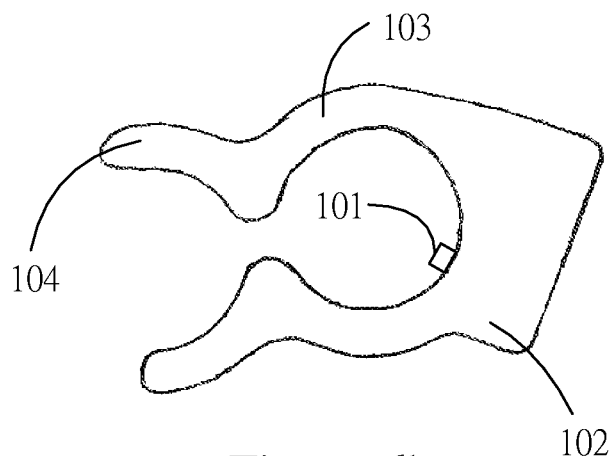
Figure 6C:
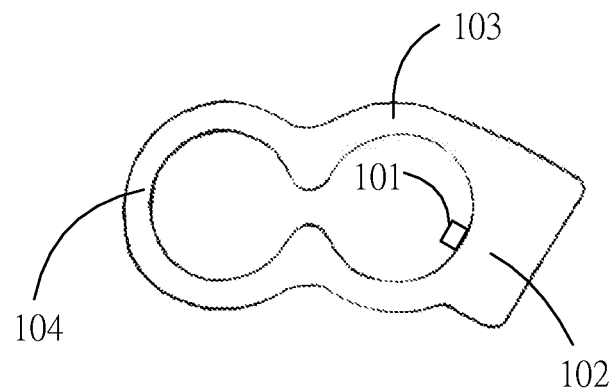

FIGS. 6a-c illustrate three types of the wearable device 100 with different shapes of the matching unit 104, according to alternative embodiments. In FIG. 6a, the matching unit 104 comprises two extending units being symmetrically configured at the lateral side of the main body 103 for coupling with the adjacent finger. In FIG. 6b, the matching unit 104 comprises two extending units being configured at the lateral side of the main body 103 with an offset towards the adjacent finger, in order to fit the shape and structure of the adjacent finger. With such configuration, during the long-term wear of the wearable device 100, especially during sleep, the user will feel more comfortable. In FIG. 6c, the configuration of the matching unit 104 to the main body 103 is similar to FIG. 6b but the matching unit 104 is a loop with or without an opening for coupling with the adjacent finger. As understood by one skilled in the art, the embodiments given in FIGS. 6a-c are examples and not intended to limit the structure and mechanism of the main body 103 and the matching unit 104. In one embodiment, the wearable device 100 further comprises a processing unit coupled with the sensor 101 for data processing. In an alternative embodiment, the sensor 101 is able to communicate with an outside processor or server for data processing via wired or wireless transmission.

In one embodiment, the wearable device 100 includes a functional component 102, as shown in FIG. 1. Optionally the functional component 102 may be detachable such that it may be mounted on and detached from the main body 103 of the wearable device 100. As such, the user may easily replace the main body 103 with another size to fit the fingers of different people while using the same functional component 102. In order to mount the sensor 101 on a proper surface of the finger, i.e., being close to the palmar surface 322 of the finger 105 with a certain offset from the lateral side, i.e., 20 degrees to 50 degrees, the functional component 102 with the sensor 101 attached to the main body 103 is properly configured such that when the wearable device 100 is worn on the user's finger 105, the functional component 102 is close to the lateral side of the finger 105. In one embodiment, the functional component 102 is operable to guide the user to properly wear the wearable device 100 at the proper position. For example, when the wearable device 100 is worn on the index finger and the functional component 102 protrudes toward the thumb, the shape of the functional component 102 is designed to match the shape of the thumb as well as the relationship between the index finger and the thumb, in order to guide the user to properly wear the wearable device 100 at the proper position.

Figure 7:
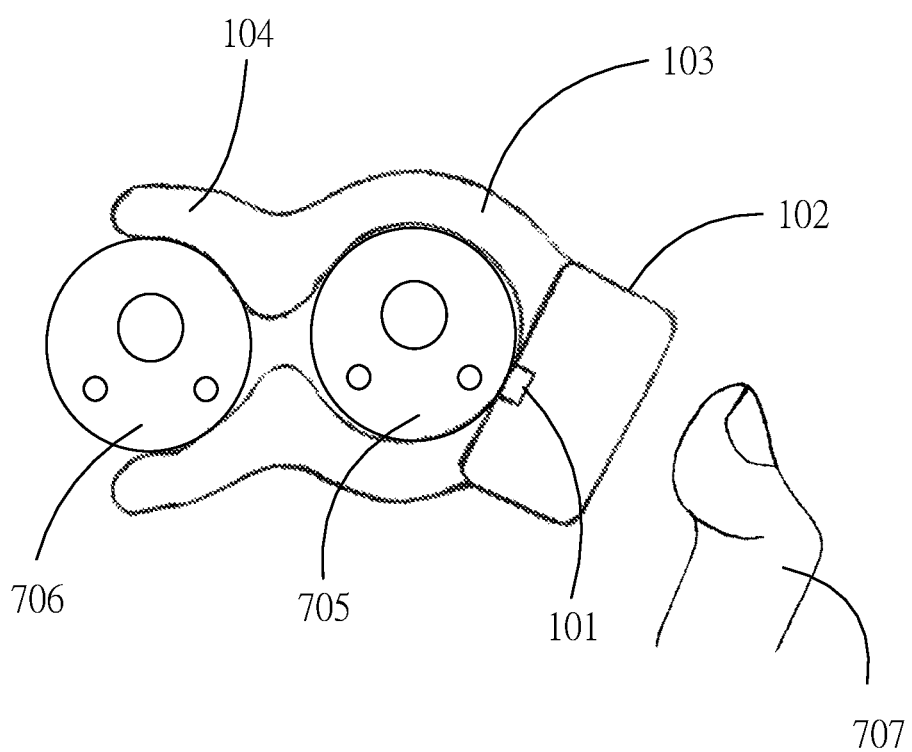
FIG. 7 shows a preferred wearing manner for the wearable device 100, according to one embodiment.

FIG. 7 shows a preferred wearing manner for the wearable device 100, according to one embodiment. FIG. 7 is described in combination with FIG. 1. When wearable device 100 is worn on an index finger 105 via the main body 103, the functional component 102 is placed towards the thumb 707 and the top surface of the functional component 102 is aligned with the lateral side of the thumb 707 for guiding the user to properly wear the wearable device 100 at the proper position. In a preferred embodiment, the wearable device 100 is worn on the proximal phalange of the index finger 705 for easy and comfortable wear. Furthermore, the matching unit 104 is coupled with the adjacent finger 706 in order to align the wearable device 100 to the proper position and reduce the rotation of the wearable device 100 around the index finger 705 during long-term wear and measurement, especially during sleep.

In one embodiment, the wearable device 100 further comprises a pressure control configuration to control the pressure between the wearable device 100 and the finger.

Figure 8A:
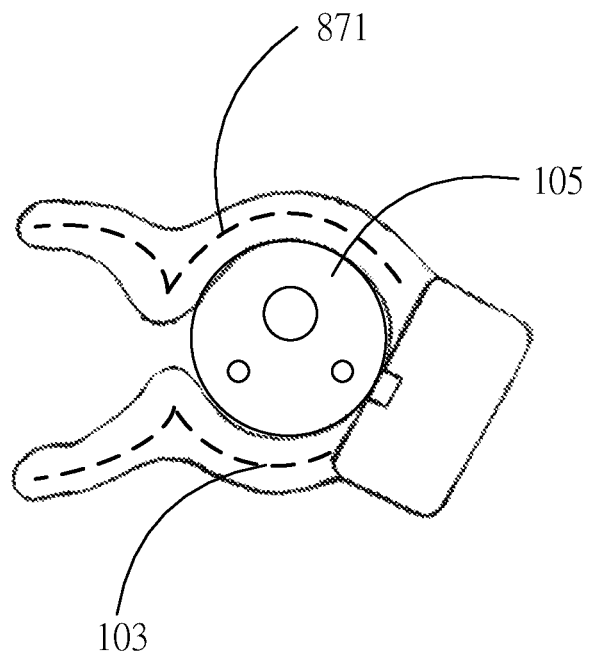
FIG. 8a shows a schematic drawing of a wearable device with a pressure control unit, according to one embodiment.
Figure 8B:
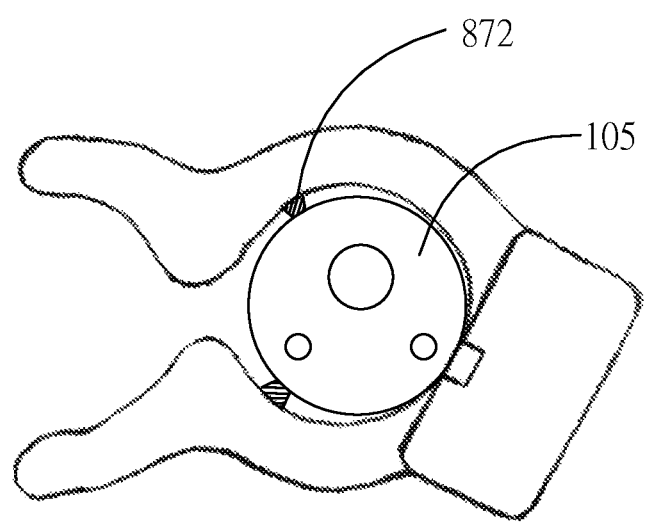
FIG. 8b shows a schematic drawing of a wearable device with another pressure control unit, according to an alternative embodiment.

During use, if the wearable device 100 is worn on the finger too tightly, it will block the blood flow and affect the accuracy of measurement. If the wearable device 100 is worn on the finger too loosely, light leakage will occur which may affect the measurement accuracy. FIG. 8a shows a schematic drawing of the wearable device 100 with a pressure control unit, according to one embodiment. FIG. 8b shows a schematic drawing of the wearable device 100 with another pressure control unit, according to an alternative embodiment. FIGS. 8a-b are described in combination with FIG. 1. The embodiments given in FIGS. 8a and 8b are examples and do not limit the structure and mechanism of the pressure control unit. As shown in FIG. 8a, a bendable unit 871 with a predetermined coefficient of deformation is embedded into the main body 103 and/or the matching unit 104 for fitting with different finger sizes. When the wearable device 100 is worn on the finger 105, the bendable unit 871 will provide a clamping pressure within a proper range on the finger 105. As shown in FIG. 8b, one or more protrusions 872 are configured on the inner surface of the main body 103. In one embodiment, at least one protrusion 872 is made by an elastic material. In another embodiment, the main body 103 is, at least partially, made from an elastic material. When the wearable device 100 is worn on the different fingers with different sizes, the wearable device 100 with the protrusion(s) 872 will provide a pressure within a proper range on the finger 105. In other embodiment, the tightness of the wearable device 100 is adjustable and further comprises a pressure sensor to sense the pressure between the wearable device 100 and the finger 105. If the pressure sensor detects the pressure is higher than a first threshold or lower than a second threshold, the tightness of the wearable device 100 will be adjusted automatically or manually by the user.

Figure 9A:
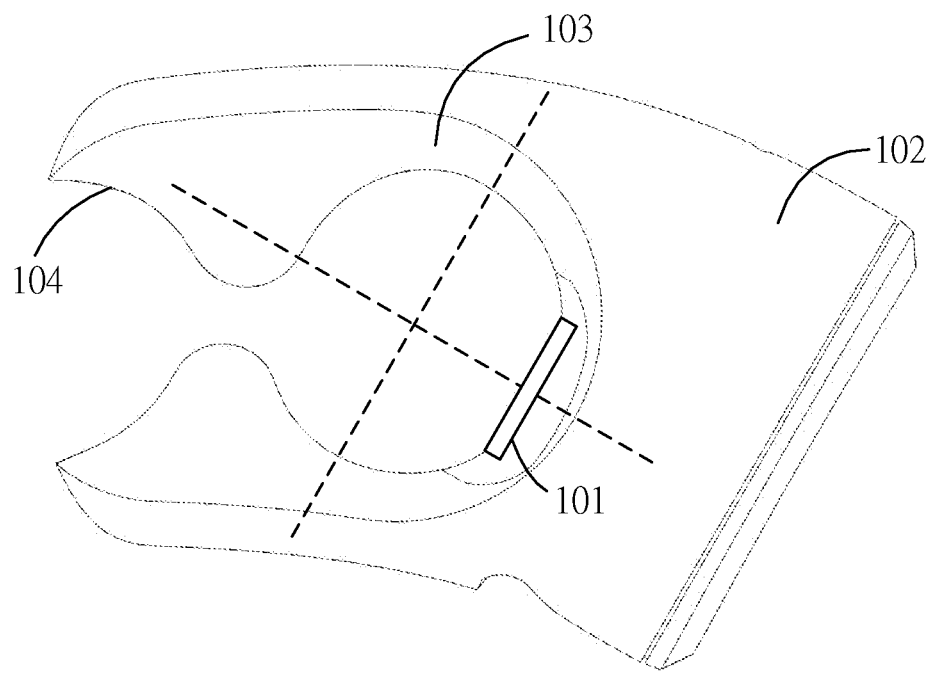
FIGS. 9a and 9b show side views of the wearable device with a pressure control unit, according to one embodiment.
Figure 9B:
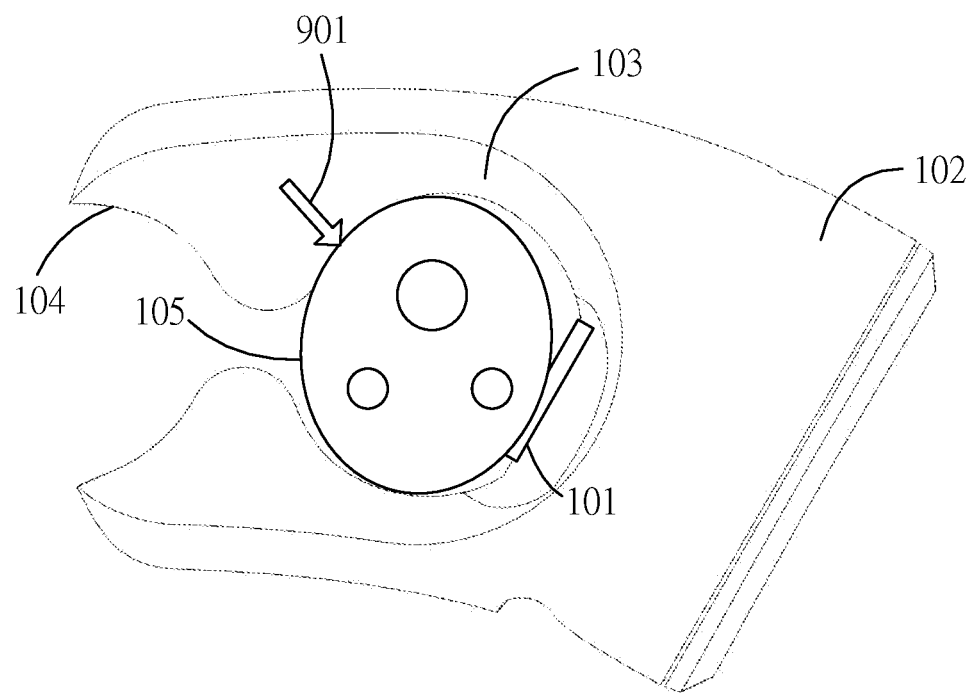

FIG. 9a illustrates a schematic drawing of the wearable device 100 with pressure control configuration, according to one embodiment. FIG. 9b illustrates how the pressure control works on the finger when the wearable device 100 is worn on the finger, according to the subject embodiment. FIGS. 9a-b are described in combination with FIG. 1. As shown in FIG. 9a, the main body 103 comprises a loop structure configured such that a force is generated to press the finger against the sensor 101 when the wearable device 100 is worn on the finger.

Furthermore, different from the conventional pulse oximeter worn on the fingertip, the wearable device 100 is designed to be worn on a base of the finger. Since the space between the bases of two fingers are much smaller than that between the fingertips, the shape of the main body 103 may be designed to generate a force on the finger towards the sensor 101 while not affecting the movement of the adjacent fingers, when the wearable device 100 is worn on the finger. In one preferred embodiment, the main body 103 is made of deformable materials and the loop structure of the main body 103 is in an ellipse shape with an axis being arranged in a predetermined direction in order to generate the target force on the finger towards the sensor 101 when the wearable device 100 is worn on the finger. In a more specific embodiment, the axis of the ellipse shape of the loop structure passes through the sensor 101.

When a finger is inserted into the main body 103 of the wearable device 100 as shown in FIG. 9b, the special shape of the main body 103 will be slightly distorted against the finger and enable the finger to be attached to the sensor 101. A force 901 as indicated by the arrow is generated on the finger due to the distortion of the main body 103 against the finger. Therefore, the finger is urged to be tightly attached to the sensor 101 so as to avoid the light leakage and prevent the effect of ambient light.

In one embodiment, the functional component 102 is at least partially fabricated from rigid material for supporting and protecting internal functional units, e.g., PCB and sensor 101, while the main body 103 and/or the matching unit 104 are flexible to fit different finger sizes. In one embodiment, for the functional component 102, the rigid layer is disposed inside as a housing of the internal functional units and a flexible layer covers the rigid layer to protect the rigid layer during use.

During the assembly process of the wearable device 100, in one embodiment, the rigid layer of the functional component 102 is formed firstly, and then flexible material is molded on the rigid layer to form the protection layer and is further extended to form the main body 103 and the matching unit 104. Thereafter, the functional units including the sensor 101 are assembled inside the rigid housing and waterproof material is disposed on the edge of the sensor 101. The detecting surface is exposed to the exterior through an aperture in the housing in order to detect the physiological information of the user via the attached finger. Thus, the functional units are sealed in a waterproof manner.

In an alternative embodiment, the outside protection layer of the functional component 102, the main body 103 and the matching unit 104 are initially formed integrally by a flexible material. Afterwards, adhesive material is injected around the internal surface of the protection layer to form the rigid layer as the housing of the functional units. Thereafter, the functional units including the sensor 101 are assembled inside the rigid housing while the detecting surface of the sensor 101 is exposed to the outside through a housing aperture.

In one embodiment, the wearable device 100 further comprises a wireless communication unit operable for transmitting data from the wearable device 100 to an outside device, e.g., a base station server, by way of a wireless radio frequency (RF) link using a proprietary or non-proprietary protocol. In one embodiment, the wireless communication unit comprises a Near Field Communication (NFC) chip for the communication. During operation, when the wearable device 100 is brought close to a certain electronic device, e.g., a smart phone, the electronic device will detect the wearable device 100 via the wireless communication unit and trigger the wearable device 100 to measure the health information of the user via the finger. Furthermore, the wearable device 100 will transfer the measurement result to the electronic device for further processing, recording, and/or display via the wireless communication unit. In one embodiment, the wireless communication unit stores an identification information (ID) of the user and transmits the health information with the user's ID to the electronic device without additional action of inputting user information. In an exemplary embodiment, when an electronic device installed with a specified application (APP) detects the wearable device 100 close to it, the electronic device will trigger the measurement of the wearable device 100 via the APP. The measured health data of the user is then transmitted from the wearable device 100 to the APP for further processing. In one embodiment, the APP will upload the measurement result to a Cloud or a database for further processing.

In one embodiment, a fingerprint authentication unit is integrated in the functional component 102, e.g., to configure a fingerprint authentication function on the main panel of the functional component 102. A person who intends to use the wearable device 100, must pass the fingerprint authentication by pressing a finger, e.g., thumb, onto the main panel of the functional component 102. If the person passes the authentication, he/she will be allowed to access or enable the wearable device 100 for normal measurement.

Figure 10:
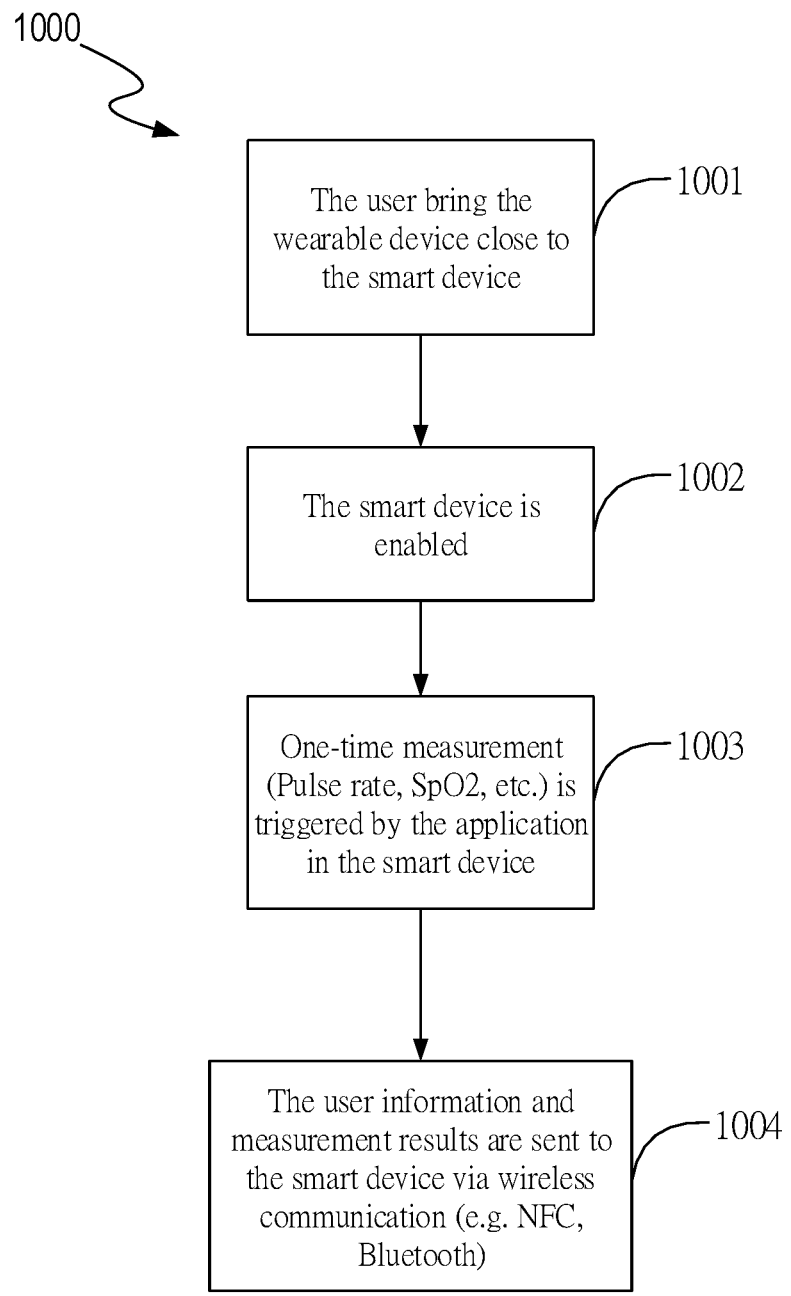
FIG. 10 shows an operation flowchart 1000 of a wearable device with a wireless communication unit, according to one embodiment.

FIG. 10 shows an operation flowchart 1000 of the wearable device 100 with a wireless communication unit, according to one embodiment. FIG. 10 is described in combination with FIG. 1. During the operation, when the user brings the wearable device 100 close to an electronic device, e.g., when the user wearing the wearable device 100 holds up a smart phone, in step 1001, the electronic device is enabled for further processing in step 1002. Then in following step 1003, the electronic device will trigger the wearable device 100 to measure the health information of the user, e.g., pulse rate and/or PPG signal and/or blood oxygen saturation and/or stress, for one or more times. Finally, the electronic device receives the measured health information with the user ID from the wearable device 100 and displays the measurement result to the user in step 1004. During operation, the electronic device will check whether a previous measurement has been completed for a pre-determined period. If yes, the electronic device will trigger the wearable device 100 to start a next measurement. Otherwise, the electronic device will suspend the trigger until reaching the pre-determined period.

In one embodiment, the wireless communication unit is a passive electronic component with low power consumption. With the communication between the wireless communication unit and the external electronic device, the wearable device 100 is triggered to start the measurement without pressing any button once the wearable device 100 is close to the electronic device. As such, the user interface of the wearable device 100 is simplified especially for elderly users and the power consumption of the wearable device 100 will be reduced. In one embodiment, the wireless communication unit with an electronic key is operable to electronically lock and/or unlock the electronic device.

In one embodiment, the wearable device 100 further comprises a motion sensor to detect the motion of the user. In one embodiment, when the user is awake, the wearable device 100 will be enabled to measure the health data under predetermined conditions for saving power, e.g., triggered by the electronic device once the wearable device approaches it as described above. When the user falls asleep, since many serious symptoms, e.g., obstructive sleep apnea, occur unconsciously during the sleep, the wearable device 100 will enter a continuous measurement mode to continuously monitor the health status of the user. In one embodiment, the motion sensor comprises an accelerometer and/or a gyroscope to detect the movement, posture, and/or orientation of body of the user, e.g., lying on a horizontal plane, standing straight, or how a user's hand is placed. When the wearable device 100 is worn on the finger of the user, the motion sensor will detect whether the user is in a sleeping posture, e.g., lying on a horizontal plane without moving, or still awake, e.g., standing straight or moving. If the motion sensor detects the user is in a sleeping posture without any movement during a predetermined time period, it is determined that the user is asleep and the wearable device 100 will start to continuously measure the heart rate of the user. During sleep, when abnormal symptoms, e.g., obstructive sleep apnea (OSA), occur, the heart rate may suddenly increase and the blood oxygen saturation may accordingly decrease, which will negatively impact the user's health. If a heart rate is detected over a normal threshold $T_{HR}$, the wearable device 100 will start measuring the blood oxygen saturation of the user at once. The normal threshold $T_{HR}$ is set based on the heart rate of the user under normal breathing, e.g., the normal threshold $T_{HR}$ is 10% greater than the average heart rate under normal breathing.

Figure 11:
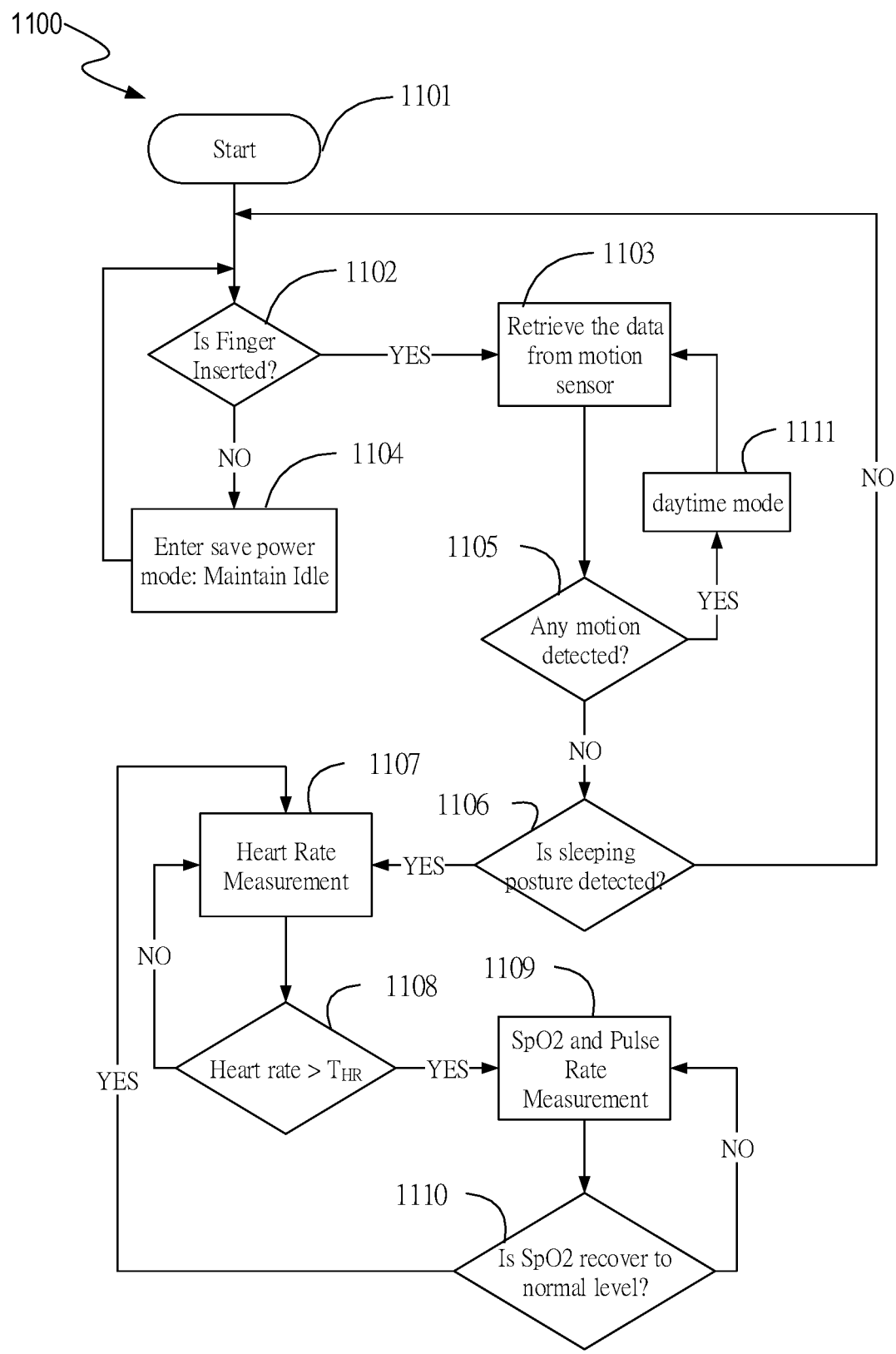
FIG. 11 shows an operation flowchart 1100 of a wearable device, according to one embodiment.

FIG. 11 shows an operation flowchart 1100 of the wearable device 100, according to one embodiment. FIG. 11 is described in combination with FIG. 1. When the wearable device 100 is enabled in step 1101, the wearable device 100 will keep detecting whether a finger is inserted into the wearable device 100 in step 1102. If yes, the wearable device 100 will begin to collect the motion data of the user from the motion sensor in step 1103. Otherwise, the wearable device 100 will remain idle without any measurement in a power-saving mode while maintaining monitoring of the finger insertion in step 1104. After the wearable device 100 collects the motion data from the motion sensor in step 1103, if no movement is detected within a predetermined period in step 1105, the wearable device 100 will further determine whether a sleeping posture is detected in step 1106. Otherwise, the wearable device 100 will enter a daytime mode 1111 to discontinuously measure the health data of the user under certain conditions, e.g., triggered by the outside electronic device, and keep monitoring the movement of the user in step 1103. In step 1106, if the user is detected in a sleeping posture, the wearable device 100 will enter a sleep mode and start continuously measuring and recording the heart rate of the user in step 1107. Otherwise the wearable device 100 will return to step 1102 for detecting whether a finger is inserted into the wearable device 100. During step 1107, if the wearable device 100 detects that the measured heart rate exceeds the normal threshold $T_{HR}$ in step 1108, the wearable device 100 will start to further measure and record the blood oxygen saturation, as well as the heart rate, in step 1109. Otherwise, the wearable device 100 will keep monitoring and recording the heart rate in step 1107. During step 1109, if the measured blood oxygen saturation is higher than a predetermined threshold $T_{BOS}$, that means the blood oxygen saturation has returned to normal level in step 1110, the wearable device 100 will return to step 1107. Otherwise, the wearable device 100 will keep monitoring and recording the blood oxygen saturation and heart rate in step 1109.

With such a configuration, the efficiency of the wearable device 100 will be increased and the power consumption thereof will be reduced. Firstly, the motion sensor is adopted to monitor the posture, body orientation, and/or motion of the user, in order to control the measurement under different conditions to save power. Secondly, the power consumption of the blood oxygen saturation measurement is relatively high when compared with the pulse rate measurement. Since an abnormal condition of the blood oxygen saturation occurs in connection with a sudden increase in the heart rate, the wearable device 100 will start to measure the blood oxygen saturation once the heart rate is higher than the threshold Tim, so as to minimize the power consumption.

In one embodiment, the wearable device 100 is operable to determine the sleep cycle of the user based on the measured health information. When people fall asleep, they will experience rapid eye movement (REM) sleep and non-REM sleep through the sleep in various cycles. The beginning stage of the sleep cycle, N1 includes non-REM sleep as it prepares the body to shut down. During this stage, people can be easily awakened by noise or thoughts. The middle stage involves light sleep, N2 usually lasting anywhere for about 10-25 minutes. Non-REM sleep always happens in this stage. Deep sleep, N3 always occurs in a later stage during which activity in the body is low and activity in the brain is very high. REM sleep usually happens in the last stage of the sleep cycle for about 70-90 minutes after a deep sleep phase N3. REM sleep is the stage of sleep when dreaming occurs. When awoken from this stage, a person may feel disoriented. In order to avoid waking up the user during the REM stage, resulting in disoriented condition, it's preferred to wake up the user in a light stage of the sleeping cycle, e.g., in a non-REM stage such as stage N1, to make the user feel more energetic and comfortable.

During operation, when the wearable device 100 detects that respective increments of the heart rate and the heart rate variability of the user are greater than respective predetermined thresholds, it is determined that the user is in the non-REM stage, e.g., stage N1. In order to avoid a disoriented condition caused by waking up the user during the REM stage, the user will be woken up, e.g., by a morning call, when he/she is determined to be in the non-REM stage. In a preferred embodiment, the wearable device 100 further comprises a temperature sensor to detect the user's body temperature. When the wearable device 100 detects the respective increments of the heart rate, heart rate variability and the body temperature of the user are greater than respective predetermined thresholds, it is determined that the user is in a lighter sleep stage. By adding the parameter of the body temperature, the determination of the light sleep stage will be more accurate.

Figure 12:
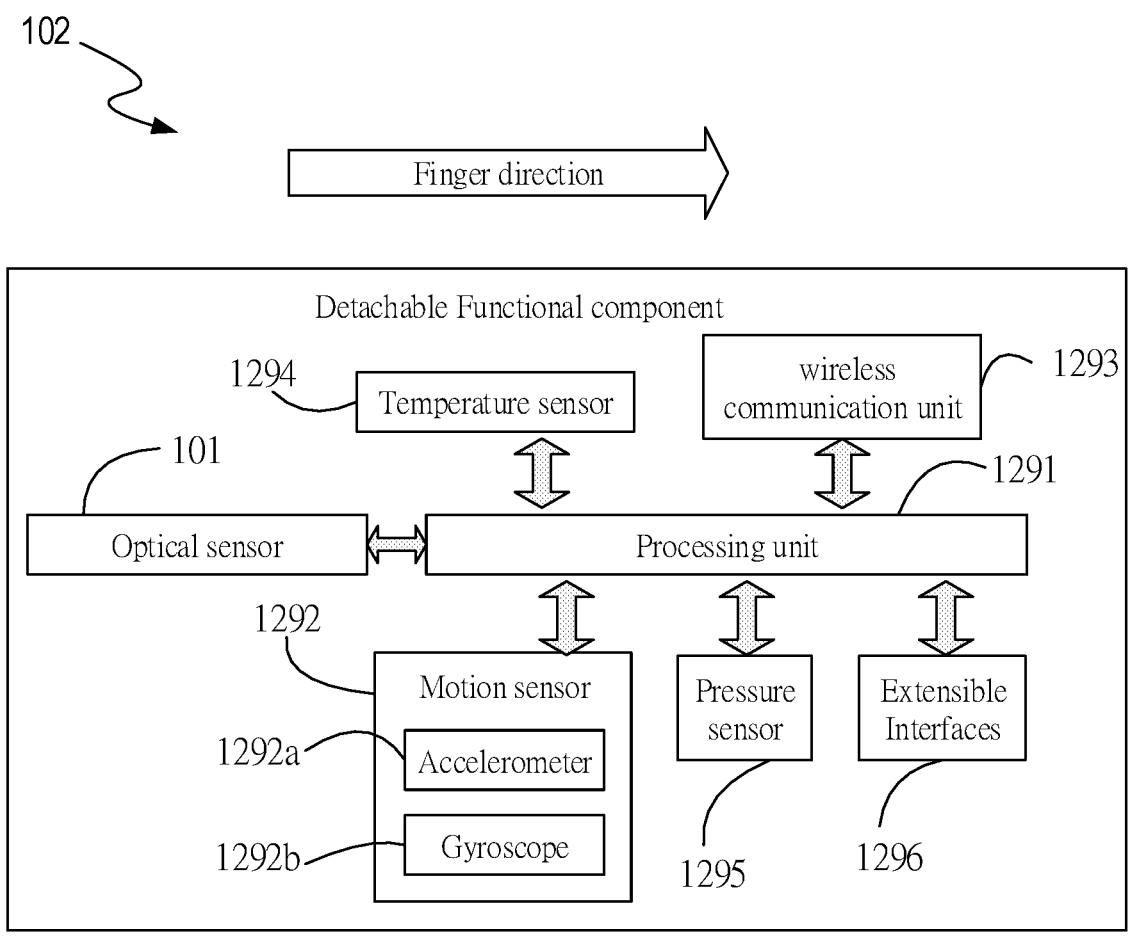
FIG. 12 is a schematic structure of the functional component of a wearable device as described above, according to one embodiment.

FIG. 12 is a schematic structure of the functional component 102 of the wearable device 100 as described above, according to one embodiment. FIG. 12 is described in combination with FIG. 1. As shown in FIG. 12, the functional component 102 comprises the sensor 101 being placed along the longitude direction of the finger, and a processing unit 1291 coupled to the sensor 101 to receive the measured health information of the user for further processing, including, but not limited to, health status analysis, stress analysis, and sleeping quality analysis. In one embodiment, the functional component 102 may further comprises a motion sensor 1292 to detect the movement, body orientation, and/or posture of the user. Based on the detection result from the motion sensor 1292, the processing unit 1291 will decide whether or not to trigger the continuous measurement of the sensor 101. Furthermore, the functional component 102 may comprise a wired or wireless communication unit 1293 for communicating with one or more external electrical devices via wired or wireless transmission, a temperature sensor 1294 to sense the body temperature of the user for healthcare, a pressure sensor 1295 to sense the pressure between the wearable device 100 and the finger for better pressure control, and one or more extensible interfaces 1296 operable to connect with one or more external functional units for function extension. It should be understood to one of ordinary skill in the art that the elements and configuration of the functional component 102 given in FIG. 12 are for illustration purpose and not limited to one embodiment. In other words, the functional component 102 may comprise more or fewer or different functional units and the layout of the functional units is alterable.

Figure 13:
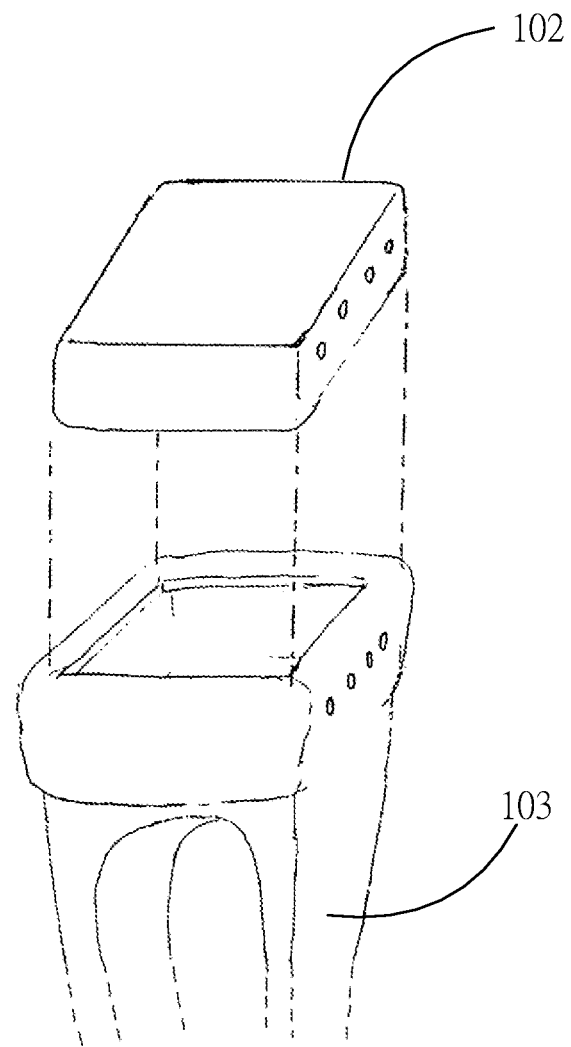
FIG. 13 illustrates a structure of a wearable device with a detachable functional component, according to one exemplary embodiment.

FIG. 13 illustrates a structure of the wearable device 100 with a detachable functional component 102, according to one exemplary embodiment. As shown in FIG. 13, the functional component 102 is able to be detached from and mounted on the main body 103. The main body 103, or further with matching unit 104, are partially omitted with a dashed line and may be any available shape and not limited to the illustration in FIG. 13. With the detachable structure, the user may easily replace the main body 103 from one size to another size to fit the fingers of different people while using the same functional component 102. Furthermore, the detached functional component 102 can be removed, stored, and used for activity tracking in daytime, in one embodiment.

During operation, there are several external functional units operable with the wearable device, e.g., an augmented wireless communication unit, interactive unit, memory, weight scale, spirometer, etc., so that the size of the wearable device may be significantly reduced while supporting various functions. In one embodiment, the wearable device is able to identify which external functional unit is plugged in so as to activate the functionality automatically.

Figure 14A:
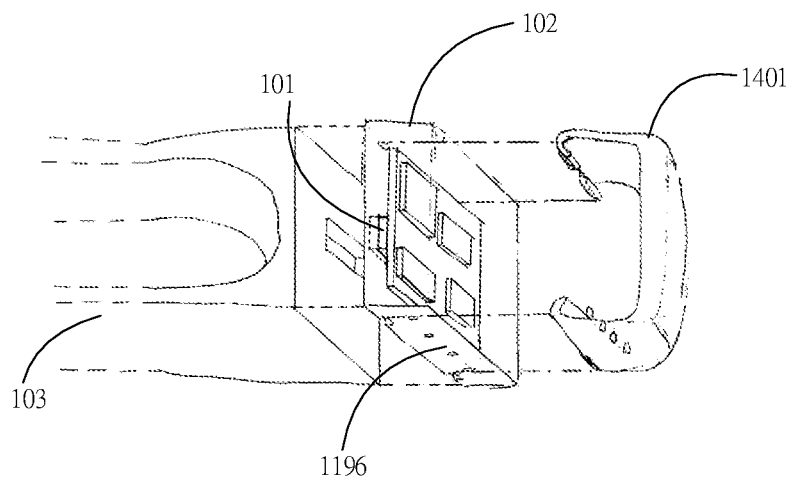
FIG. 14a illustrates a structure of a wearable device with one or more extensible interfaces for extending functionalities, according to one embodiment.

FIG. 14a illustrates a structure of the wearable device with one or more extensible interfaces for extending functionalities, according to one embodiment. FIG. 14a is described in combination with FIG. 1 and FIG. 12. As shown in FIG. 14a, the detachable functional component 102 of the wearable device 100 comprises a sensor 101 and several functional units as illustrated in FIG. 12, which are configured in a predetermined layout. The functional component 102 further comprises one or more extensible interfaces 1296 for receiving one or more external functional units 1401.

In one embodiment, the functional component 102 comprises a plurality of pins for connecting with the external functional units 1401. When one external functional unit 1401 is plugged in the functional component 102, the external functional unit 1401 will connect to a respective set of the pins in a particular manner. For example, for the interactive unit, the 1st and 2nd pins will be connected; for the wireless communication unit, the 3rd and 4th pins will be connected; and for the memory, the 1st and 3rd pins will be connected. By connecting the external functional unit to a respective set of pin(s), the functional component 102 is able to identify the external functional unit 1401 based on the connected pin(s). In an alternative embodiment, when the external functional unit 1401 is plugged into the wearable device 100, the functional component 102 will fetch the identification information in an analog or digital manner from the external functional unit 1401 via the external interface 1296 to identify it. As compared to the previous embodiment of identifying the external functional units 1401 via corresponding pin connection, the configuration of the external interface 1296 in this embodiment is simple and seamless. However, the wearable device 100 may identify the external functional units 1401 quicker in the previous embodiment.

Additionally, similar to FIG. 13, the main body 103, or further with matching unit 104, are partially omitted with a dashed line as they may be any available shape and not limited to the illustration of FIG. 14a.

Figure 14B:
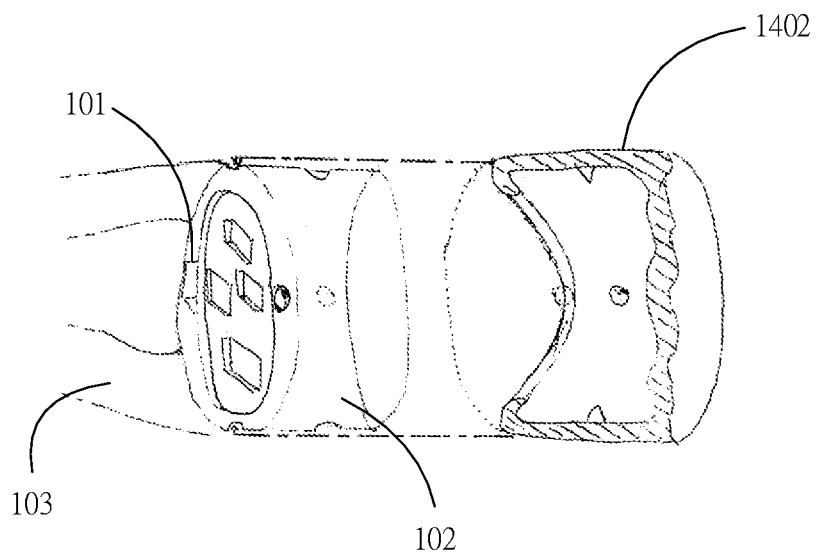
FIG. 14b illustrates a structure of a wearable device with external interface for extending functionalities, according to another embodiment.

FIG. 14b illustrates a structure of the wearable device with external interface for extending functionalities, according to another embodiment. FIG. 14b is described in combination with FIG. 1 and FIG. 12. As shown in FIG. 14b, an external integral functional unit 1402 including several functional sub-units is connectable to the functional component 102 of the wearable device 100. When the external integral function unit 1402 is connected to the functional component 102, the external integral function unit 1402 is configured to activate a target functional sub-unit according to a predetermined manner. In one embodiment, the external integral function unit 1402 is able to rotate at several predetermined angles, e.g., 90, 180, and/or 270 degrees, to enable the corresponding sub-units. With different angular configurations, the functional component 102 will identify which sub-unit is enabled and activate the corresponding sub-unit accordingly. In an alternative embodiment, the external integral functional unit 1202 further comprises a selection panel to select the sub-units and inform the wearable device 100 of the selection.

In one embodiment, a docking station for storing the wearable device 100 is operable for supporting several functions, including but not limited to, a battery charger of the wearable device 100, a portable battery bank being operable for charging not only the wearable device 100 but also other electronics, e.g., smart phone, a wake-up alarm based on the monitoring result of the sleeping cycle by the wearable device 100, an abnormal state alarm for abnormal conditions/symptoms, and/or multi-media player with control based on the monitoring result of the sleeping status of the user. For example, if the wearable device 100 detects the user is in a sleep posture and the heart rate is lower than a sleeping threshold $T_{SLP}$, it is determined that the user is asleep. Then the multi-media player will be turned off for maintaining silence and power saving. The sleeping threshold $T_{SLP}$ is determined based on the heart rate of the user under normal breathing, e.g., the sleep threshold $T_{SLP}$ is 10% smaller than an average heart rate under normal breathing. Furthermore, since the battery of the wearable device 100 is limited due to the compact size, it is important to charge the wearable device 100 periodically. In one embodiment, when the wearable device is stored in the docking station, the wearable device will be charged automatically via the battery charger by the internal battery bank or by outside power. In one embodiment, the docking station is designed to deactivate the wake-up alarm function by putting the wearable device 100 into the docking station for charging, in order to ensure the wearable device 100 is charged by the docking station after long term use during the night. Furthermore, the docking shape is specially designed to help the user to check whether the wearable device 100 is worn on the proper finger in a proper manner.

Figure 15:
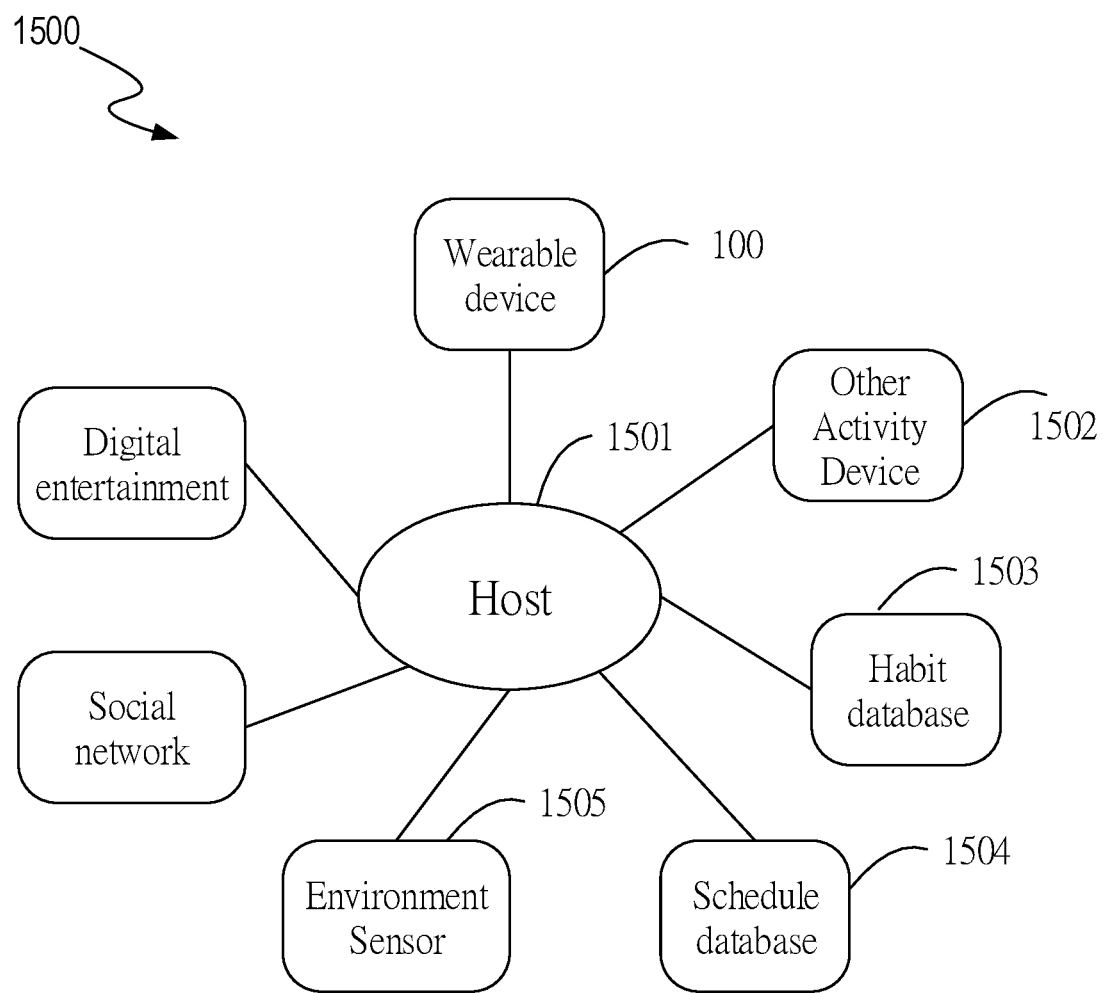
FIG. 15 shows a schematic drawing of an application system 1500 for a wearable device, according to one embodiment.

FIG. 15 shows a schematic drawing of an application system 1500 for the wearable device 100, according to one embodiment. In the application system 1500, the wearable device 100 is able to communicate with a station server 1501 via wired or wireless transmission. During operation, the wearable device 100 transmits the monitoring data to the station server 1501 for further processing, e.g., cloud computing and analysis. The application system 1500 also comprises other functional nodes to get and/or store other data of the subject, e.g., health information from a wristband or other wearable device, habits of the user from the habit database 1503, a schedule list of the user from the schedule database 1504, and/or environment data from the environmental sensor 1505. Based on the data collected, the station server 1501 can perform analysis and provide recommendations/tips to the users.

Figure 16:
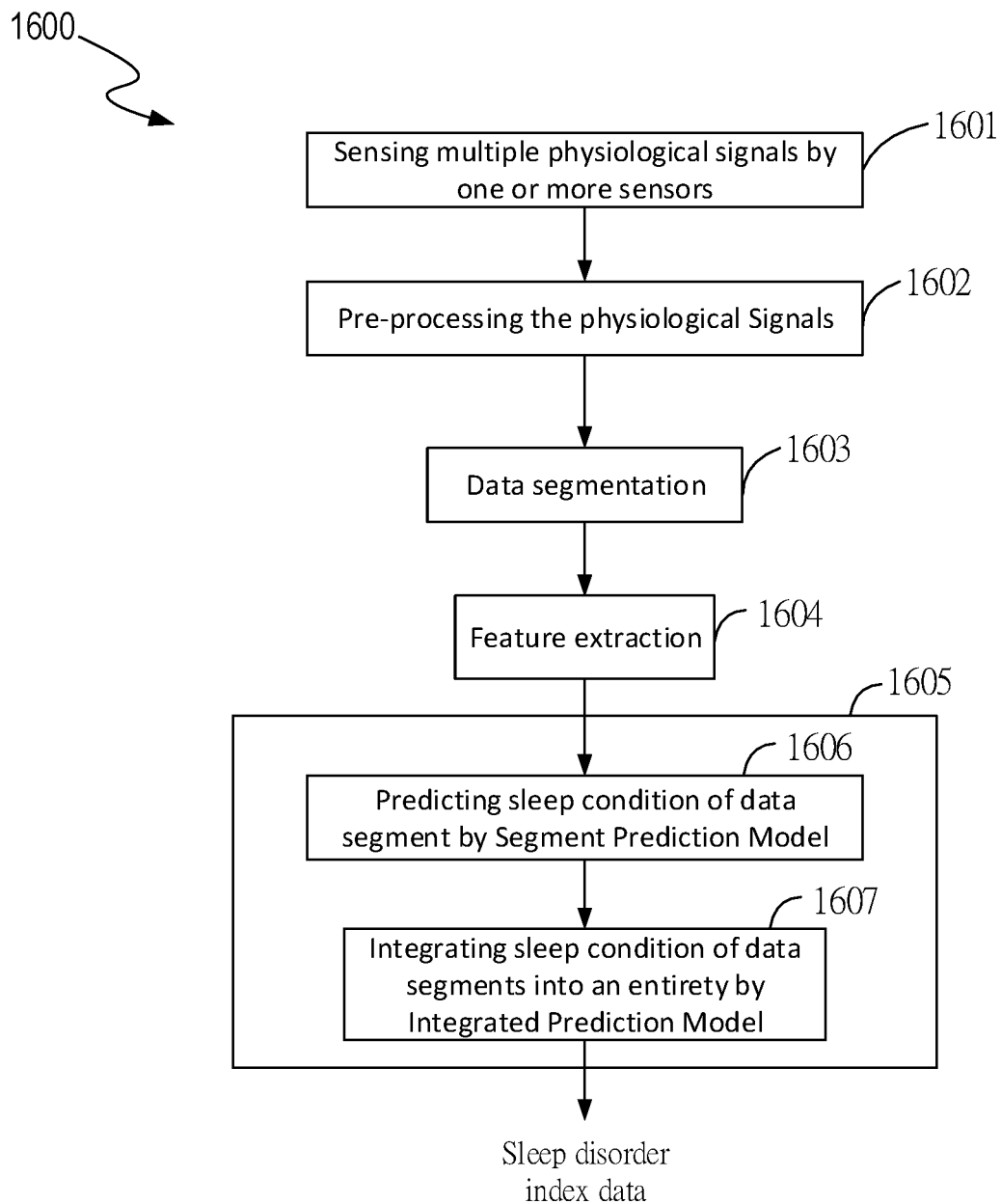
FIG. 16 is a flowchart 1600 for evaluating a sleep condition, according to one embodiment.

Recently, an increasing number of people have a sleep disorder problem during sleep which may seriously interfere with normal physical, mental, social and emotional functioning. Under such condition, it is necessary to monitor and track sleep conditions during the entire period of sleep so as to diagnose and/or prevent serious disease at an early stage. FIG. 16 shows an operation flowchart 1600 for evaluating the sleep condition with the wearable device 100, according to one embodiment. FIG. 16 is described in combination with FIG. 1. The sleep condition may contain occurrences and severities of a sleep disorder and the sleep status.

During operation, multiple physiological signals for evaluating the sleep condition (thereinafter as "evaluation signals") are sensed by one or more sensors in step 1601. In one embodiment, the evaluation signals may include cardiovascular and/or motion signals. In one embodiment, the cardiovascular signals may include, but not limited to, blood oxygen saturation signal (SpO2), SpO2 variations, heart rate, heart rate variations, and/or PPG waveform. In one embodiment, the one or more sensors may include, but are not limited to, the optical sensor and motion sensor of the wearable device 100. In step 1602, the physiological signals are pre-processed by multiple pre-processors. In one embodiment, the pre-processing operations may include, but are not limited to, filtering, re-calculating, and/or transforming the respective physiological signals. In step 1603, the processed signal data is segmented into several segments. In one embodiment, the processed signal data is time-serially segmented into a sequence of discrete segments. In a preferred embodiment, the processed signal data is divided into shorter segments whose time periods are within a range of 10-30 minutes. In a specific embodiment, the processed signal data is divided into shorter segments of equal time periods. In a more specific embodiment, the processed signal data is divided into multiple segments for every 15-minute time interval. By timely dividing the processed signal data into several shorter segments whose time periods are within 10-30 minutes, the evaluation result of the sleep condition based on the segmented data may be more accurate.

Thereafter, in step 1604, a plurality of features are extracted from the segmented data by analysis. In one embodiment, the features are extracted from the physiological data based on a predetermined feature extraction algorithm to map the physiological data into a reduced set of variables or features to summarize the information in the recording. In one embodiment, the extracted features measure relevant properties of the physiological signals for further evaluation processing. The extracted features are then sent to an evaluation model used to evaluate the sleep condition. More specifically, in one embodiment, the extracted features of the data segments are input into a segment evaluation model to evaluate the occurrences of sleep disorder, e.g., occurrences of hypopnea and apnea, the severities of sleep disorder, e.g., oxygen desaturation levels, and the sleep status, corresponding to each data segment, e.g., the data segment during every 15-mins time interval. Thereafter, the evaluation result of the data segments is sent to an integrated evaluation model to integrate the evaluation result of the data segments into an entirety that indicates sleep conditions over the entire measurement. The evaluated sleep condition will be output as sleep disorder index data, e.g., apnea-hypopnea index and/or oxygen desaturation index, used for further diagnosis.

In one embodiment, the physiological signals of the user measured by the wearable device 100 are sent to the remote host, server, cloud and/or database for recording, analysis and diagnosis based on the evaluation model predefined therein. Furthermore, the evaluation model may be periodically updated with the newly measured signals so as to achieve a more accurate evaluation result.

Figure 17:
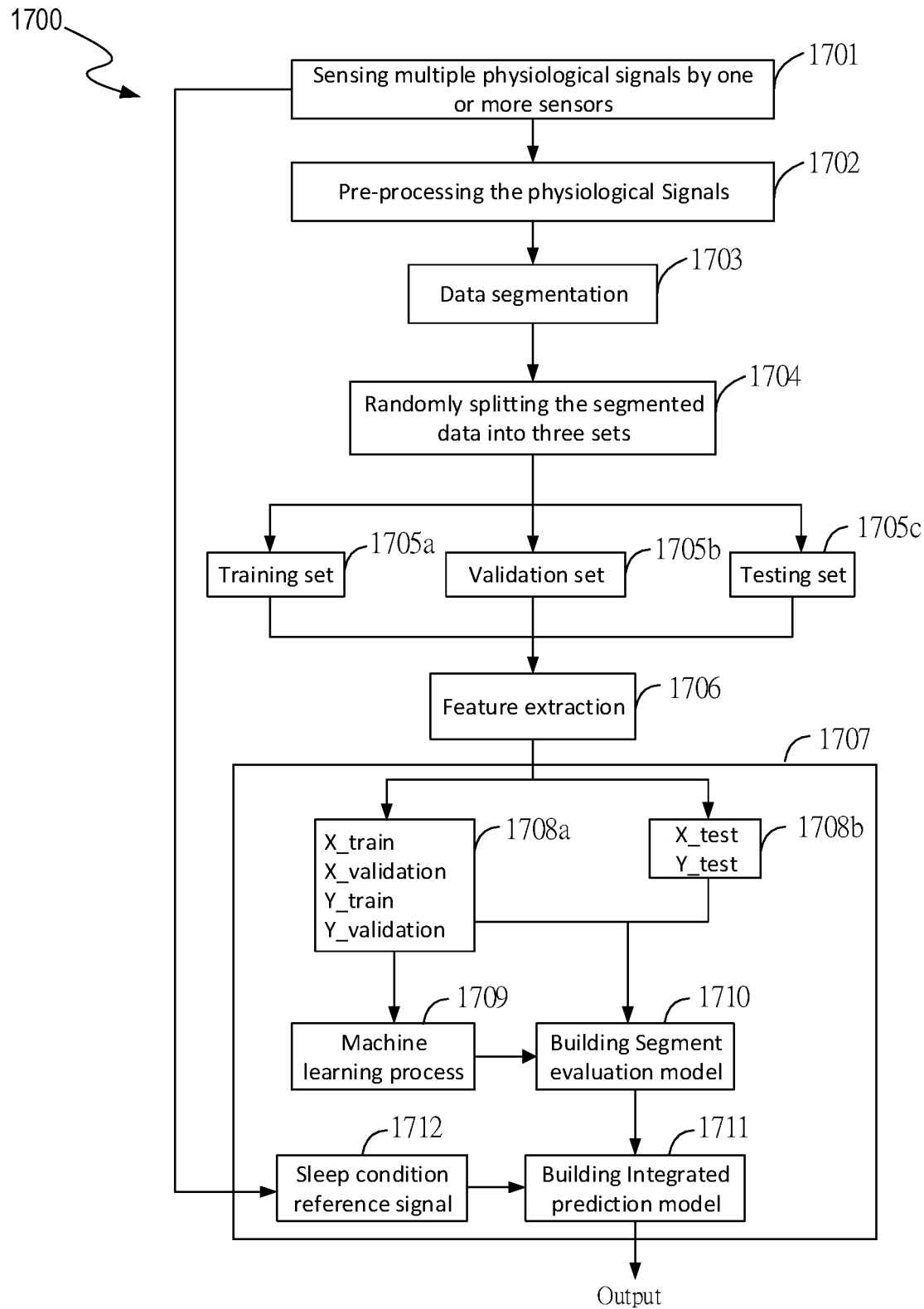
FIG. 17 is a flowchart 1700 of depicting the building of an evaluation model operable for evaluating a sleep condition, according to one embodiment.

FIG. 17 shows an operation flowchart 1700 for building the evaluation model operable for evaluating the sleep condition, in accordance with one embodiment. FIG. 17 is described in combination with FIG. 1 and FIG. 16. During operation, multiple physiological signals are sensed by one or more sensors in step 1701. In one embodiment, the multiple physiological signals may include, but are not limited to, a first group of signals for evaluating the sleep condition, i.e., evaluation signals, and a second group of signals indicating the sleep condition as a reference (thereinafter "reference signals"), wherein the evaluation signals may include the cardiovascular and/or motion signals, and the reference signals may include standard polysomnography signals. The reference signals may include manually and/or automatically labelled annotations of respiratory events and/or sleep status. In one embodiment, the one or more sensors may include, but are not limited to, the wearable device 100 and sensors used in standard polysomnography, e.g. EEG, EMG, EOG, ECG and nasal airflow sensors. In step 1702, the physiological signals are pre-processed by multiple pre-processors. In step 1703, the processed signal data is segmented into several segments.

The segmented data is randomly split into multiple sets, in step 1704. In one embodiment, the segmented data is randomly split into three sets, i.e., a training set 1705a, a validation set 1705b, and a testing set 1705c. In one embodiment, the training set contains 70% of the datasets, while the validation set contains 15% thereof and the testing set contains 15% thereof. Thereafter, in step 1706, a plurality of features is extracted from the data of the three sets by analyzing the subject data. In one embodiment, each set is applied on the same feature extraction algorithm.

In step 1707, an evaluation model used to evaluate the sleep condition is trained and built up based on the extracted features of the three sets. More specifically, features of the training and validation sets in block 1708a, i.e. X_training, Y_training, X_validation, and Y_validation are used for a machine learning process to train a machine learning model, e.g. an artificial neural network, in step 1709, with the X_training and X_validation features corresponding to the evaluation signals and Y_training and Y_validation features corresponding to the reference signals. This well-trained machine learning model is the core for building a segment evaluation model in step 1710. The features of a testing set in block 1708b, i.e., X_testing and Y_testing, are used to test the performance of the developed segment evaluation model, with the X_testing features corresponding to the evaluation signals and the Y_testing features corresponding to the reference signals. In one embodiment, the output of the segment evaluation model indicates the sleep condition within the corresponding data segment.

Then the integrated evaluation model is developed based on the output of the developed segment evaluation model in step 1711 for integrating the evaluated sleep condition of the data segments into an entirety. The sleep condition reference signals in block 1712 are used to test the performance of the final integrated evaluation model in the step 1711. In one embodiment, the apnea-hypopnea index is the main parameter of reference signals for testing the performance of the integrated evaluation model. The evaluation models, including the segment evaluation model and the integrated evaluation model, are then output and applied to the operation as illustrated in FIG. 16 to evaluate the sleep condition during the entire sleep period.

In a further embodiment, the wearing size of the wearable device as illustrated above, e.g., the wearable device as shown in FIG. 7, could be adjusted with respect to different sizes of fingers.

Figure 18:
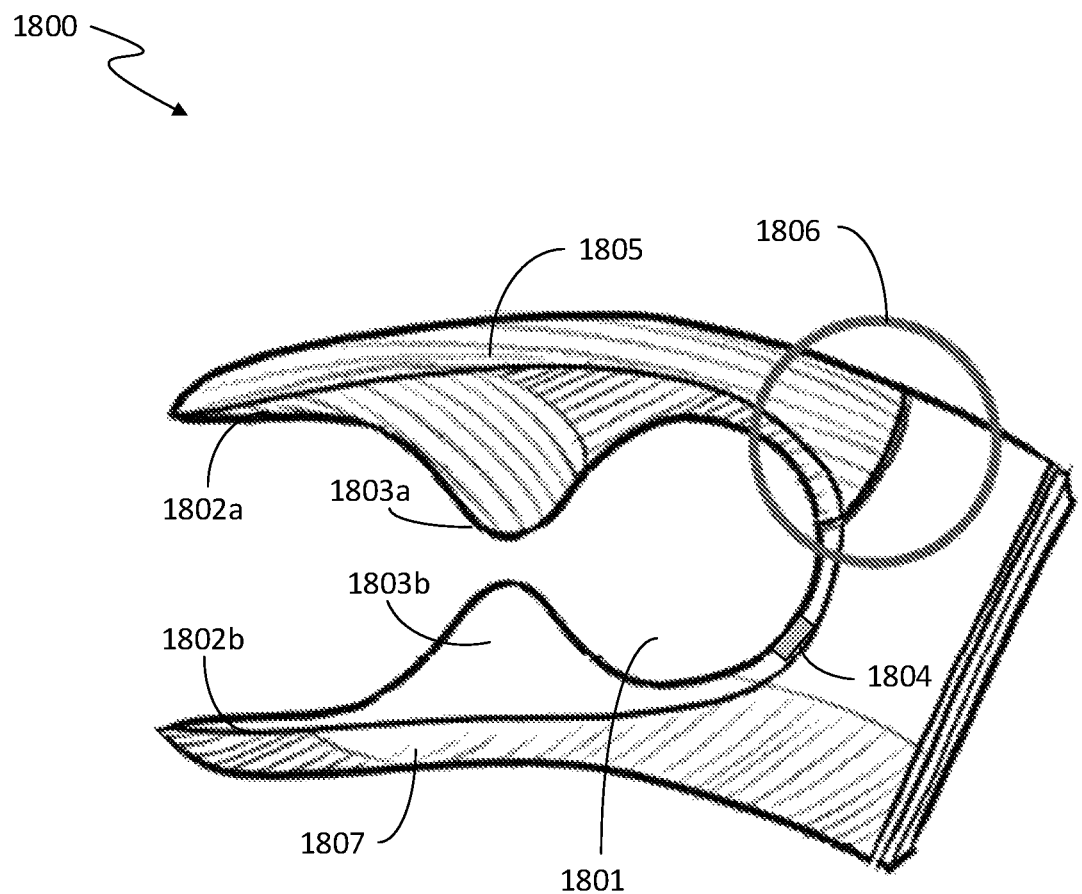
FIG. 18 shows a schematic drawing of an adjustable wearable device 1800, according to one embodiment of the present invention.

FIG. 18 shows a schematic drawing of a wearable device 1800, according to one embodiment of the present invention. As shown in FIG. 18, the wearable device 1800 is designed to be worn on a finger for measuring the physiological information of a user. In one embodiment, the wearable device 1800 is worn on the subject finger through a main body 1801 of the wearable device 1800. In a preferred embodiment, the subject finger is an index finger. In addition, two wings 1802a and 1802b extended from the main body 1801 is operable to hold a finger adjacent to the subject finger, e.g., the middle finger, for eliminating unwanted rotation of the wearable device 1800. Two protrusions 1803a and 1803b protruded respectively from an upper portion 1805 and a lower portion 1807 help to define a wearing size of the main body 1801 for enforcing the subject finger to be close to a sensor 1804, which is operable to detect the user's physiological information at the finger. In one embodiment, the sensor 1804 includes a first light emitter to emit a first light, a second light emitter to emit a second light; and a light detector to detect the first and second light reflected from the finger for measuring physiological information of the user.

Figure 19:
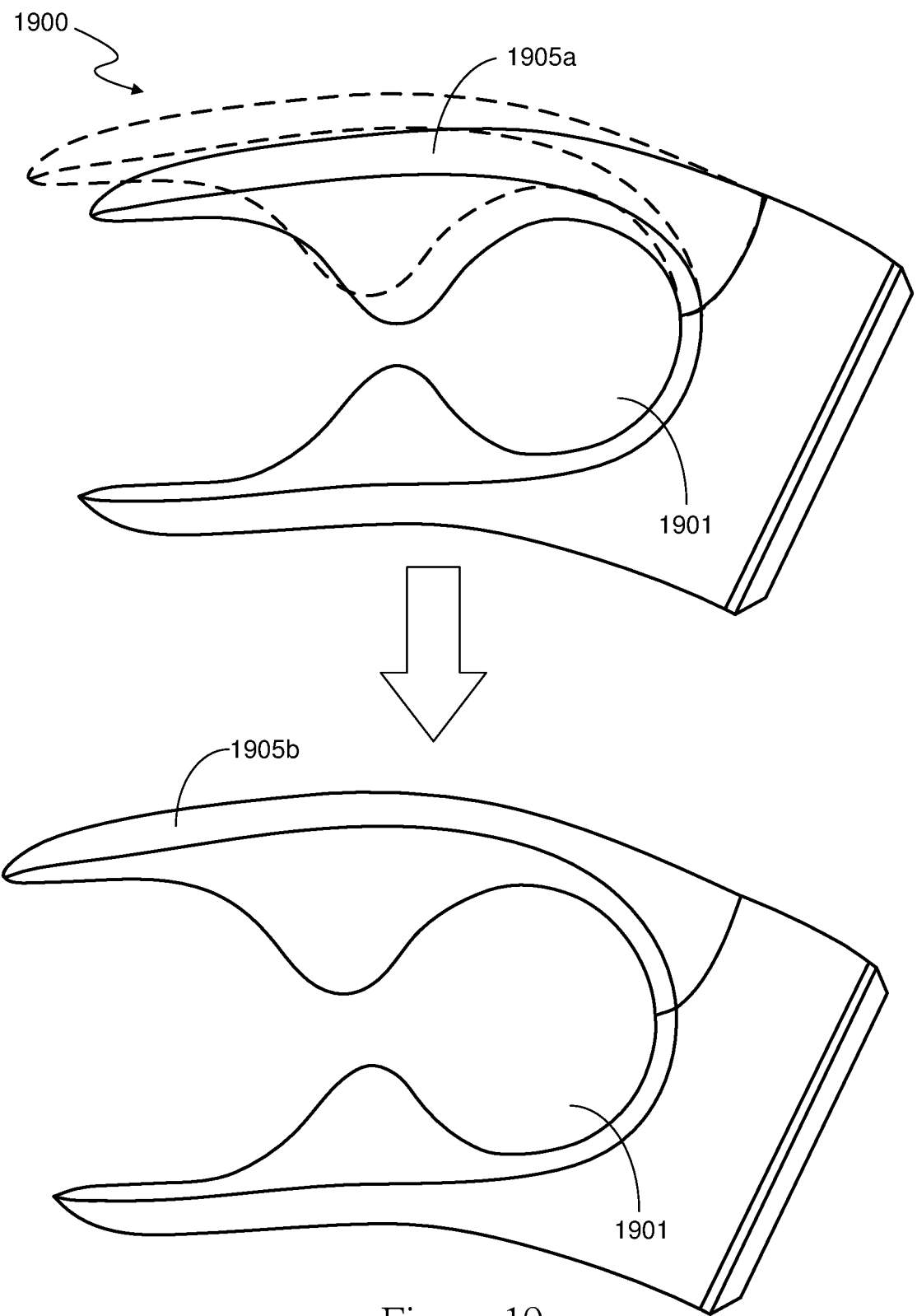
FIG. 19 illustrates an operation manner of a wearable device 1900 adjusted in different sizes, according to one embodiment of the present invention

In one embodiment, the upper portion 1804 of the wearable device is configured to be detachable from and attachable to the wearable device 1800, as specified by a circle 1806. By changing different sizes of the upper portion 1804, the wearing size of the main body 1801 could be adjusted to fit for different fingers. FIG. 19 illustrates a schematic structure of a wearable device 1900 adjustable in different sizes, according to one embodiment of the present invention. As shown in FIG. 19, when the upper portion 1905a of the wearable device 1900 is replaced with a bigger type of upper portion 1905b, the wearing size of the main body 1901 in the lower device is enlarged accordingly to accommodate a bigger finger, as can be clearly seen from the comparison between upper and lower devices (for highlighting the comparison, the bigger type of upper portion 1905b is also indicated by dotted line in the upper device). Similarly, the upper portion 1905a of the wearable device 1900 could be also replaced with a smaller type of upper portion for accommodating a smaller finger, in other embodiments.

In one embodiment, the upper portion 1905 is mechanically attached to the wearable device 1900 in a clip-on manner. In another embodiment, the upper portion 1905 is mechanically attached to the wearable device 1900 by screwing the upper portion 1905 onto the wearable device 1900. In alternative embodiments, the upper portion 1905 is connected to the wearable device by other screwing methods, for example, the upper portion 1905 is connected to the wearable device 1900 by fixing one or more screws between the upper portion 1905 and wearable device 1900. In still another embodiment, the upper portion 1905 is mechanically attached to the wearable device 1900 by a tenon technique, e.g., to insert a tenon extending from the wearable device 1900 into a mortise of the wearable device 1900. In still another embodiment, the upper portion 1905 is attached to the wearable device 1900 via one or more snap buttons configured between the two parts. As can be understand by one skilled in the art, the connection methods as illustrated above are examples. The connection between the upper portion 1905 and the wearable device 1900 could be achieved in many ways while satisfying the replaceable requirement. And the connecting position between the upper portion 1905 and the wearable device 1900 is not limited to the configuration as specified by the circle 106. During the operation, if the current wearing size of the main body 1901 is not suitable for the finger of the current patient, it is demanded to replace the upper portion 1905 with a more proper one. Under such condition, a proper upper portion will be selected from different types of the upper portions after deciding the current finger size, after then it will replace the current upper portion for further user.

Figure 20:
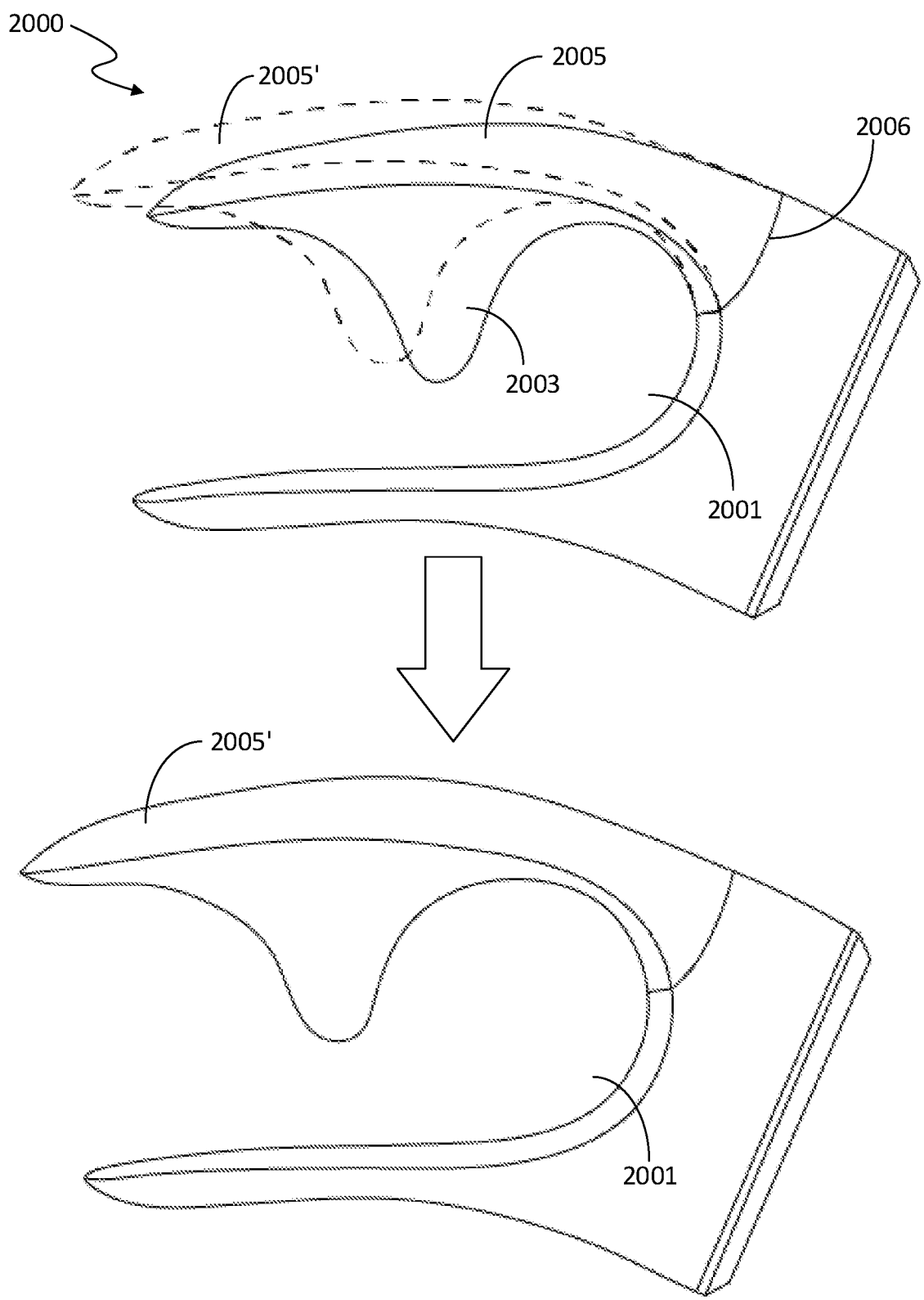
FIG. 20 illustrates an operation manner of a wearable device 2000 adjusted in different sizes, according to another embodiment of the present invention.

FIG. 20 shows a schematic drawing of a wearable device 2000 adjusted in different sizes, according to another embodiment of the present invention. As shown in FIG. 20, the wearable device 2000 has similar structure as the one shown in FIGS. 18 and 19 except that there is only one protrusion 2003 protruded from the upper portion 2005. By changing an upper portion 2005 of the wearable device 2000 at a joint coupling exemplarily indicated as 2006, the wearing size of the wearing body 2001 could be adjusted to match different fingers. Since the wearing size of the wearing body 2001 is mainly determined by the protrusion 2003 of the upper portion 2005 while the surface of the lower portion is flat, the adjustment range of the wearing size mainly defined by the upper portion 2005 could be extended and the flexibility of the replacement of the upper portion 2005 could be enhanced. In an exemplary embodiment, when the upper portion 2005 of the wearable device 2000 is replaced with a bigger type of upper portion 2005', the wearing size of the wearing body 2001 will be enlarged accordingly for accommodating a bigger finger, as can be clearly seen from the comparison between upper and lower devices (for highlighting the comparison, the bigger type of upper portion 2005' is also indicated by dotted line in the upper device). Similarly, the upper portion 2005 of the wearable device 2000 could be also replaced with a smaller type of upper portion for accommodating a smaller finger. In the subject embodiment, since the wearing size of the wearing body 2001 is mainly determined by the protrusion only protruded from the upper portion 2005, the adjustment range of the wearing size of the wearing body 2001 by changing the upper portion 2005 is relatively high. In one embodiment, under the configuration as shown by FIG. 20, eight kinds of the upper portion 2005 adapted with two kinds of the wearing body 2001 could be matched to most of the fingers. Therefore, the cost will be reduced and the matching efficiency will be improved. In one embodiment, when an upper portion is replaced with another type of the upper portion, the internal wearing shape of the wearing body 2001 will be kept in a predetermined shape, no matter which kind of the upper portion is adopted. When a finger is inserted into the wearing body 2001, a slight distortion will occur on the wearing body due to its predetermined shape, and a pressure force would therefore be applied on the inserted finger to press the finger towards the sensor direction.

Figure 21:
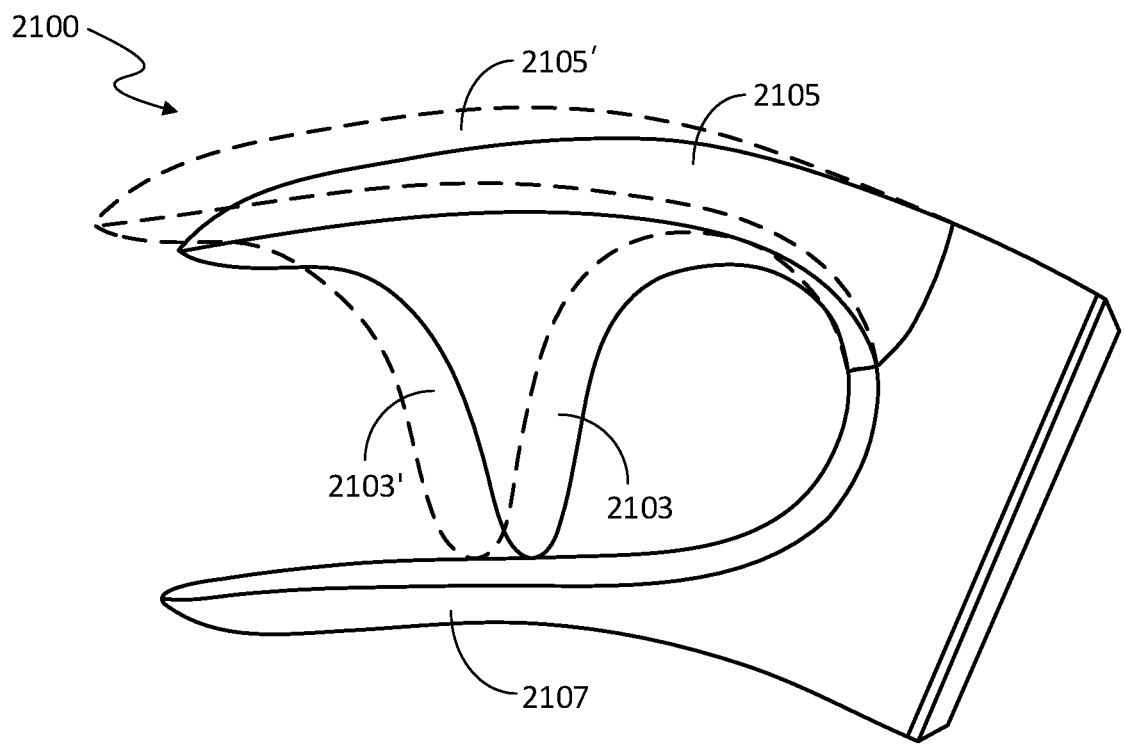
FIG. 21 illustrates a schematic drawing of an adjustable wearable device 2100 with close loop structure, according to another embodiment of the present invention.
Figure 21:
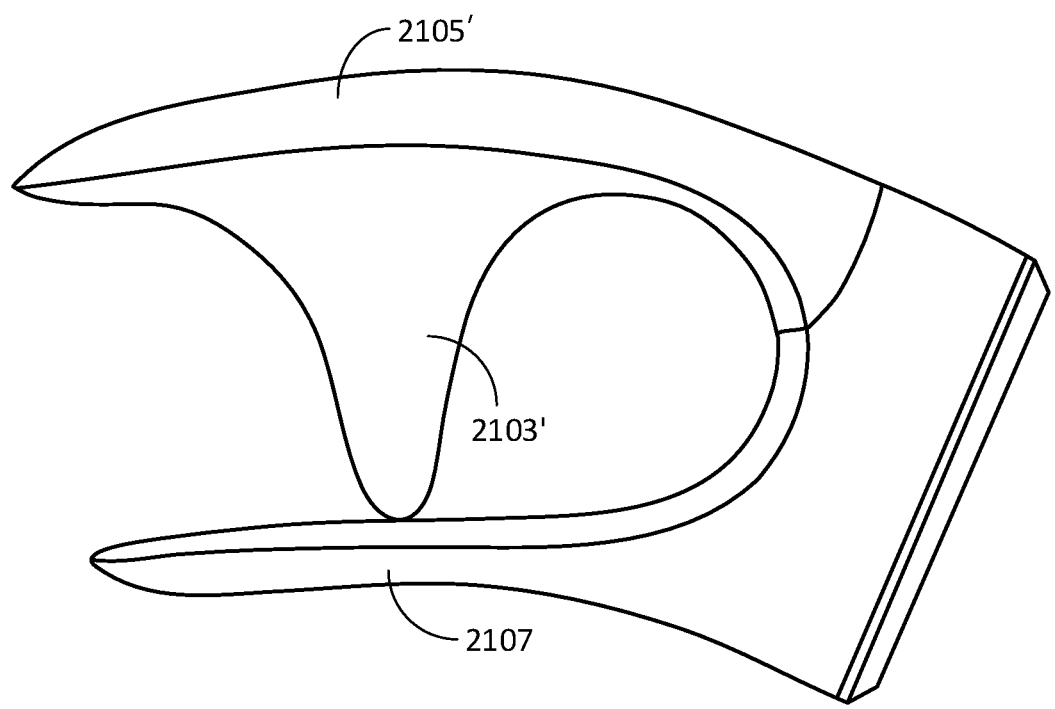

FIG. 21 illustrates a schematic drawing of an adjustable wearable device 2100 with close loop structure, according to another embodiment of the present invention. As shown in FIG. 21, the protrusion 2103 protruded from the upper wing 2105 is extended towards the lower wing 2107 and coupled to the lower wing 2107 for forming a close loop to improve the stability when the wearable device 2100 is worn on the digit. When the upper wing 2105 is replaced with another upper wing 2105' in different size, the corresponding protrusion 2103' is also extended to and coupled with the lower wing 2107 to form a close loop.

Figure 22:
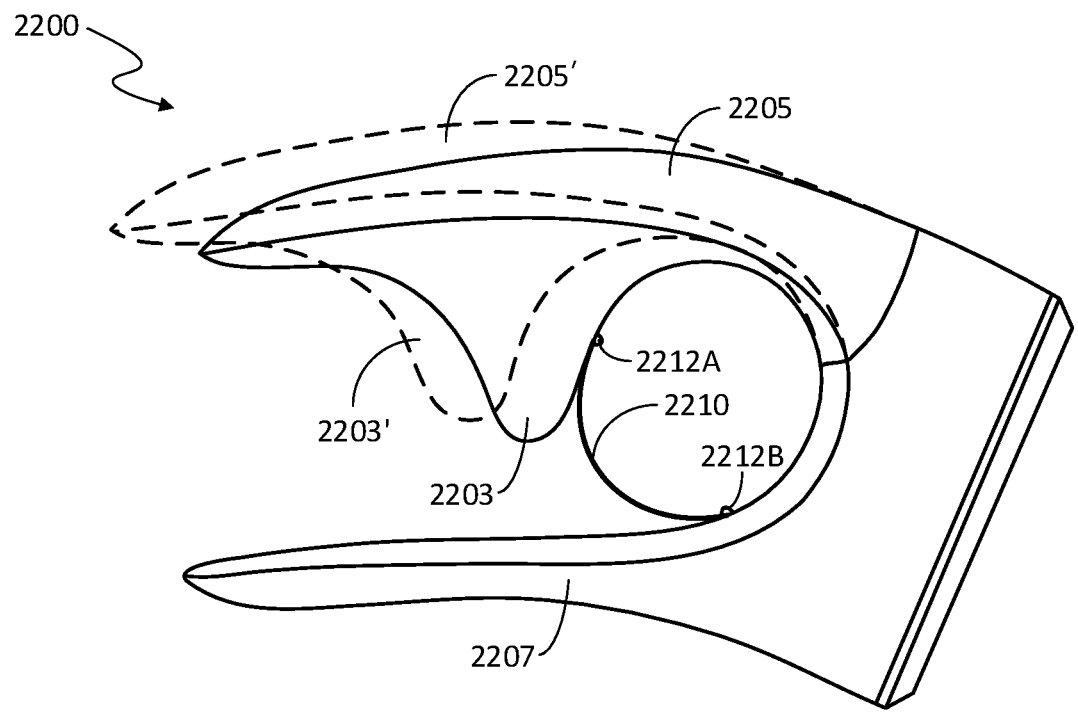
FIG. 22 illustrates a schematic drawing of an adjustable wearable device 2200 with close loop structure, according to another embodiment of the present invention.
Figure 22:
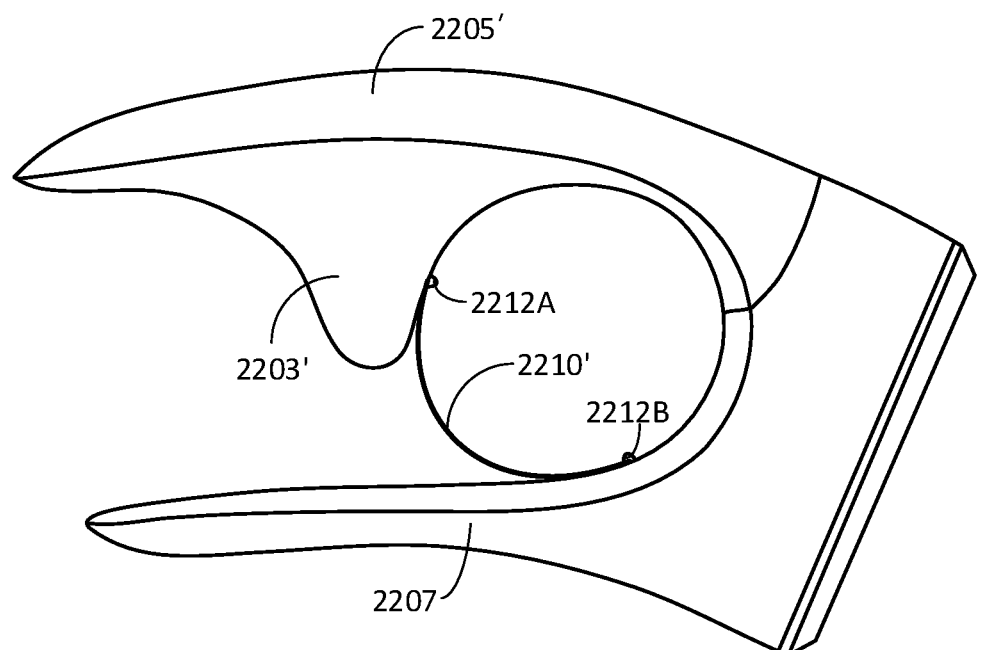

FIG. 22 illustrates a schematic drawing of an adjustable wearable device 2200 with close loop structure, according to another embodiment of the present invention. As shown in FIG. 22, a connecting unit 2210 is coupled between the upper wing 2205 and the lower wing 2207 for forming a close loop. In one embodiment, a locking unit 2212A and a locking unit 2212B are configured on the upper wing 2205 and the lower wing 2207 respectively for coupling the connecting unit 2210 between the two wings. In a preferred embodiment, the locking unit 2212A is configured on the protrusion 2203 for enhancing the user experience. When the upper wing 2205 is replaced with another upper wing 2205' in different size, another connecting unit 2210' is to be coupled between the upper wing 2205' and the lower wing 2207 for forming another close loop. In one embodiment, the connecting unit 2210 and/or 2210' could be adjusted according to different finger sizes.

Figure 23:
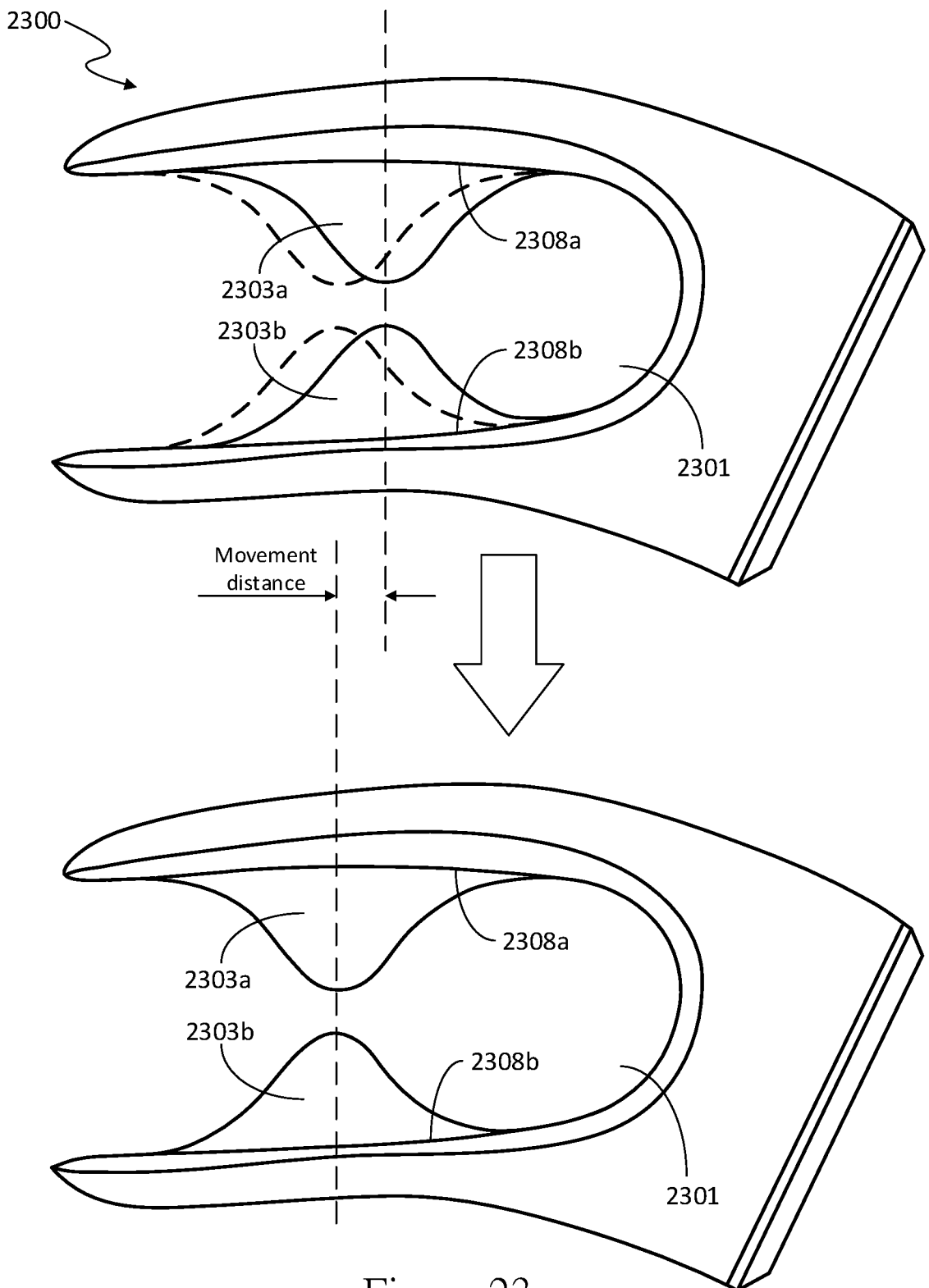
FIG. 23 illustrates an operation manner of a wearable device 2300 adjusted in different sizes, according to another embodiment of the present invention.

FIG. 23 illustrates a schematic drawing of a wearable device 2300 adjusted in different sizes, according to another embodiment of the present invention. As shown in FIG. 23, the protrusions 2303a and 2303b, both or any one of them in alternative embodiments, are movable along a corresponding internal guide 2308a/2308b of the upper/lower portion 2305/2307, so as to adjust the wearing size of the wearable device with respect to different fingers. In an exemplary embodiment, in order to enlarge the wearing size of the wearing body 2301, the protrusions 2303a and 2303b are moved along the rail guide 2308a and 2308b towards the rail direction of the wearable device 2300 in a distance as indicated between two dotted lines. As can be clearly seen from the comparison between upper and lower devices (for highlighting the comparison, the movements of protrusions 2303a and 2303b are also indicated by dotted line in the upper device), the internal wearing size of the wearing body 2301 in the lower device is enlarged accordingly for matching bigger finger. Similarly, if the protrusions 2303a and 2303b are moved along the rail guide towards the front direction, the wearing size of the wearing body 2301 is reduced accordingly for matching a smaller finger. As can be understood by one skilled in the art, the protrusions 2303a and 2303b could be separately moved along the rail guide, in different moving distances and even in different moving directions, according to different shapes of the fingers.

Figure 24:
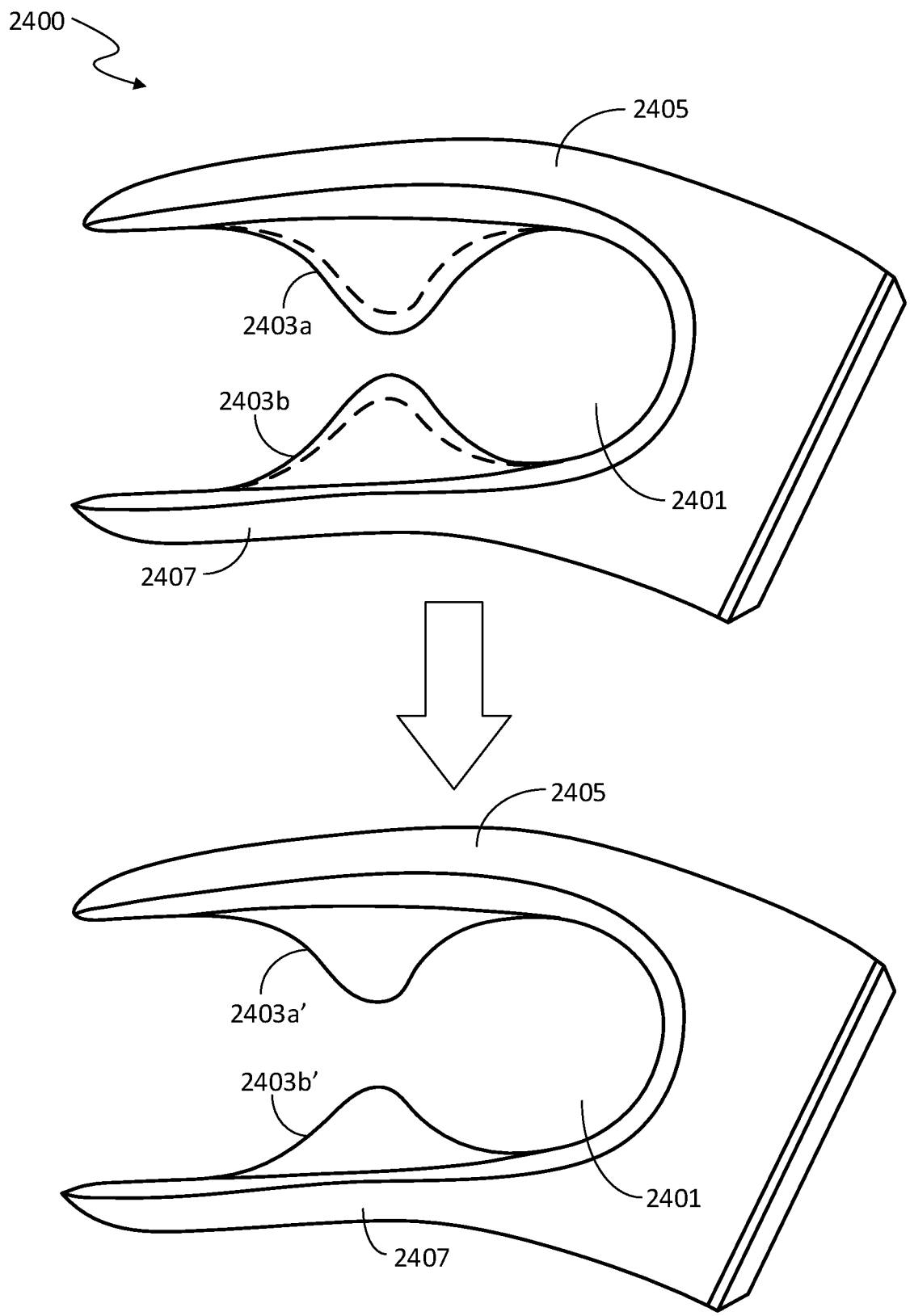
FIG. 24 illustrates an operation manner of a wearable device 2400 adjusted in different sizes, in accordance with another embodiment of the present invention.

In an alternative embodiment, the protrusion of the upper portion and the protrusion of the lower portion, both or at least one of them, could be replaced with different sizes of the protrusion candidates for adjusting the wearing size of the wearing body. FIG. 24 illustrates an operation manner of a wearable device 2400 adjusted in different sizes, in accordance with another embodiment of the present invention. As can be clearly seen from the comparison between upper and lower devices in FIG. 24, by replacing the protrusions 2403a and 2403b, both or at least one of them, in the upper device with a couple of smaller protrusions 2403a' and 2403b' in the lower device (for highlighting the comparison, the protrusions 2403a' and 2403b' are also indicated by the dotted line in the upper device), the internal wearing size of the wearing body 2401 in the lower device is enlarged for accommodating a bigger finger. Similarly, if the protrusions 2403a and 2403b in the upper device is replaced with a couple of bigger protrusions, the internal wearing size of the wearing body 2401 will be reduced accordingly for matching smaller finger.

As can be understood by one skilled in the art, the protrusions 2403a and 2403b could be replaced, together or separately, with any shape of protrusions for accommodating multiple shapes of fingers and not limited to the examples as illustrated by FIG. 24. In addition, it may be no need to replace the whole protrusion part as illustrated in FIG. 24, but may replace a portion of the protrusion according to different requirements. For example, the protrusion may be assembled by several blocks while any one of the blocks could be changed to match different shape of fingers. Furthermore, in alternative embodiments, the protrusions 2403a and 2403b can be not only replaced with different shape of protrusions, but also moved along the rail guide, so as to adjust the wearing size of the main body 2401 more flexibly and precisely. In one embodiment, at least one of the upper portion 2405, lower portion 2407 and the protrusions 2403a/2403b is made by elastic material while the others are made by rigid material for generating a pressing force upon the finger towards the sensor direction when the wearable device 2400 is worn on the subject finger.

Figure 25:
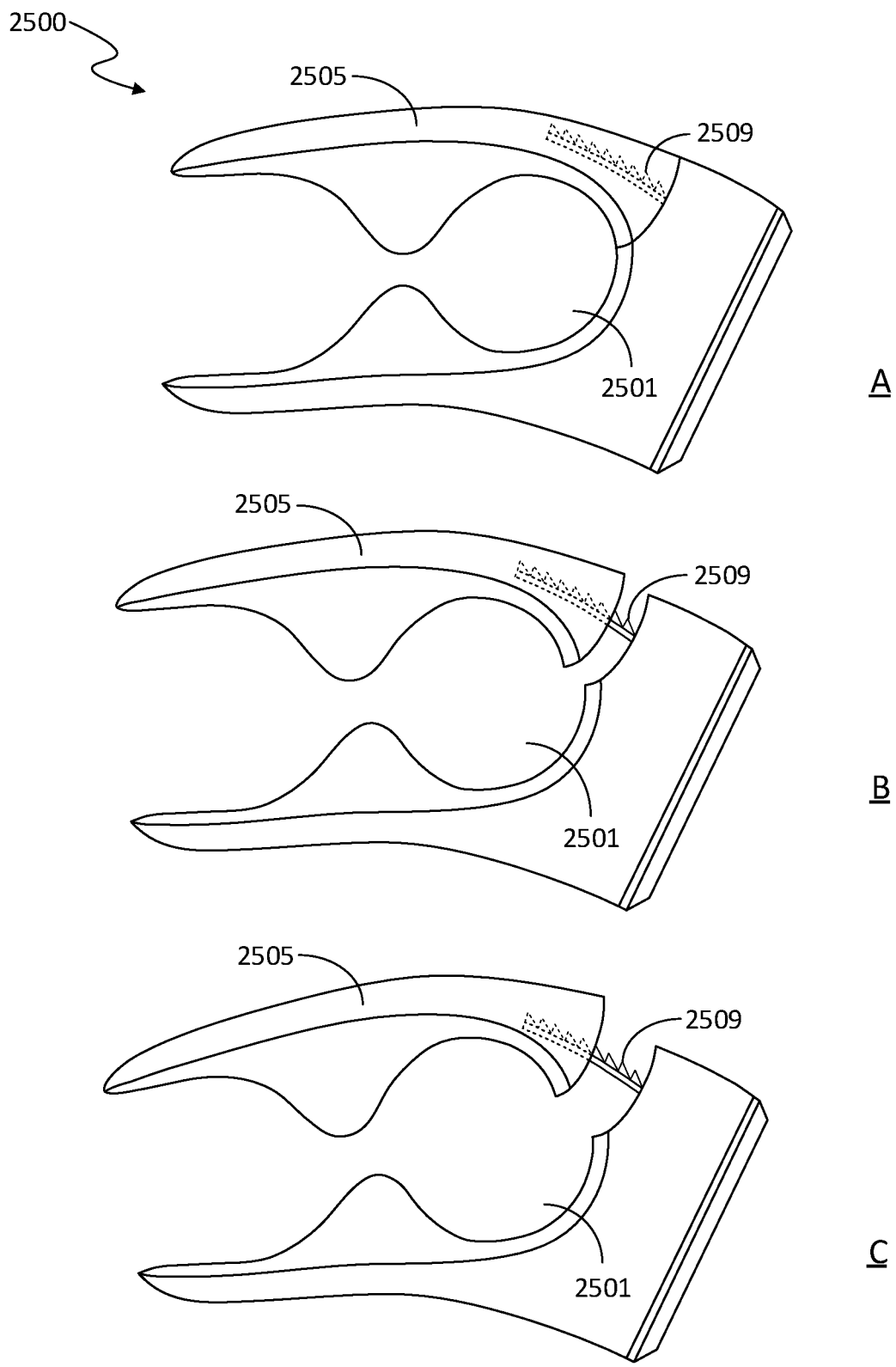
FIG. 25 illustrates a schematic drawing of a wearable device 2500 adjusted in different sizes, according to another embodiment of the present invention.

FIG. 25 illustrates a schematic drawing of a wearable device 2500 adjusted in different sizes, according to another embodiment of the present invention. As illustrated in FIG. 25, the upper portion 2505 is coupled to the wearable device 2500 via a coupling unit 2509. In one embodiment, the coupling unit 2509 is configured as a branch extended from the wearable device 2500. Zigzag pattern is configured on at least one side of the coupling unit's surface. During the operation, the upper portion 2505 could be moved along the coupling unit 2509 and locked at any position of the coupling unit 2509 by the zigzag pattern, to form a proper wearing space of the main body 2501. For example, in device B of the FIG. 25, the upper portion 2505 is moved along the coupling unit 2509 and locked at a first position of the coupling unit 2509 for matching a bigger finger. In device C of the FIG. 25, the upper portion 2505 is further moved along the coupling unit 2509 and locked at a later position for matching a much bigger finger. By properly adjust the position of the upper portion 2505 at the coupling unit 2509, the proper wearing size could be achieved.

In one embodiment, the coupling unit 2509 is integrated with the wearable device 2500 and formed by rigid material. The upper portion 2505 is formed with soft material to add an extra amount of adaptability for the main body 2501 and to generate a pressing force on the finger when it is inserted into the wearing body 2501. In further embodiment, the upper portion 2505 is detachable from the coupling unit 2509 and replaceable with another size of the upper portion, to achieve a bigger adjustment range of the wearing size of the main body 2501. As can be understand by one skilled in the art, the structure and configuration of the coupling unit 2509 is not limited to the example as illustrated in FIG. 25, but can have alternative configurations while satisfying required function to connect the upper portion 2505 with the wearable device 2500 and support the movement of the upper portion 2505 towards or away from the wearable device 2500 for the adjustment of the wearing size.

While the foregoing description and drawings represent embodiments of the present invention, it will be understood that various additions, modifications and substitutions may be made therein without departing from the spirit and scope of the principles of the present invention as defined in the accompanying claims. One skilled in the art will appreciate that the invention may be used with many modifications of form, structure, arrangement, proportions, materials, elements, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims and their legal equivalents, and not limited to the foregoing description.

The invention claimed is:

1. A wearable device for detecting physiological information of a user, comprising:
   a main body configured to be at least partially worn on a digit of a user;
   at least one physiological sensor attached to the main body for detecting physiological information of the user through the digit, the physiological sensor being operatively positioned on the main body to align with a direction of blood flow at a palmar surface below a lateral side of the digit when the main body is worn; and
   at least a first upper branch and a lower branch extending from the main body and configured for holding the digit therebetween perpendicular to a longitudinal axis of the digit while reducing the movement of the wearable device,
   wherein the lower branch is fixedly coupled to the main body,
   wherein at least a part of the first upper branch is removably and replaceably coupled to the main body, and
   wherein the first upper branch includes a first protrusion formed to separate the digit and another adjacent digit, the first upper branch with the first protrusion being removably configured to be replaceable with at least a second upper branch with a second protrusion formed to accommodate a different size of digit and separate the different sized digit and another adjacent digit.

2. The wearable device of claim 1, wherein the optical sensor comprises
   a first light emitter to emit a first light;
   a second light emitter to emit a second light; and
   a light detector to detect reflected first and second light from the digit.

3. The wearable device of claim 1, wherein the wearable device has a predetermined wearing shape such that a pressing force is generated on the digit towards the physiological sensor when the wearable device is worn on the digit.

4. The wearable device of claim 1, wherein the lower branch includes a third protrusion positionally formed thereon and aligned with the first protrusion of the first upper branch so as to separate the digit and the adjacent digit.

5. The wearable device of claim 1, wherein a connecting unit is coupled between the upper branch and the lower branch of the wearable device.

6. A wearable device for detecting physiological information of a user, comprising:
   a main body configured to be at least partially worn on a digit of a user;
   at least one physiological sensor attached to the main body for detecting physiological information of the user through the digit, the physiological sensor being operatively positioned on the main body to align with a direction of blood flow at a palmar surface below a lateral side of the digit when the main body is worn; and
   at least first and second branches coupled to the main body for holding the digit therebetween perpendicular to a longitudinal axis of the digit while reducing the movement of the wearable device,
   wherein at least a part of at least one of the first and second branches is movably coupled to the main body such that the wearable device is movably adjustable to accommodate different size of digits.

7. The wearable device of claim 6, wherein the at least one of the first and second branches is movably coupled to the main body along a predetermined path for accommodating a different size of digit.

8. The wearable device of claim 6, wherein the first branch includes a protrusion positionally formed to separate the digit and another adjacent digit.

9. The wearable device of claim 8, wherein the first branch with the protrusion is movably coupled to the main body along a predetermined path for accommodating different size of digits.

10. The wearable device of claim 8, wherein the protrusion is movably coupled to the first branch along a predetermined path for accommodating different size of digits.

11. The wearable device of claim 6, wherein each of the first and second branches has a protrusion positionally formed to separate the digit and the adjacent digit.

* * * * *